United States Patent
Kuchroo et al.

(10) Patent No.: US 10,934,352 B2
(45) Date of Patent: *Mar. 2, 2021

(54) BI-SPECIFIC ANTIBODIES AGAINST TIM-3 AND PD-1 FOR IMMUNOTHERAPY IN CHRONIC IMMUNE CONDITIONS

(71) Applicant: The Brigham and Women's Hospital, Inc., Boston, MA (US)

(72) Inventors: Vijay K. Kuchroo, Newton, MA (US); Ana C. Anderson, Newton, MA (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 447 days.

This patent is subject to a terminal disclaimer.

(21) Appl. No.: 15/803,079

(22) Filed: Nov. 3, 2017

(65) Prior Publication Data

US 2018/0051083 A1 Feb. 22, 2018

Related U.S. Application Data

(63) Continuation of application No. 14/857,402, filed on Sep. 17, 2015, now Pat. No. 9,834,607, which is a continuation of application No. 13/805,030, filed as application No. PCT/US2011/040665 on Jun. 16, 2011, now Pat. No. 9,163,087.

(60) Provisional application No. 61/356,354, filed on Jun. 18, 2010, provisional application No. 61/365,910, filed on Jul. 20, 2010.

(51) Int. Cl.
*C07K 16/28* (2006.01)
*A61K 39/395* (2006.01)
*A61K 39/00* (2006.01)

(52) U.S. Cl.
CPC .......... *C07K 16/2803* (2013.01); *C07K 16/28* (2013.01); *C07K 16/2818* (2013.01); *C07K 16/2896* (2013.01); *A61K 2039/505* (2013.01); *A61K 2039/507* (2013.01); *C07K 2317/31* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 7,470,428 B2 | 12/2008 | Kuchroo et al. | |
| 7,521,051 B2 | 4/2009 | Collins et al. | |
| 7,595,048 B2 | 9/2009 | Honjo et al. | |
| 9,163,087 B2* | 10/2015 | Kuchroo | ............ C07K 16/2803 |
| 9,834,607 B2* | 12/2017 | Kuchroo | ............ A61P 43/00 |
| 2004/0029226 A1 | 2/2004 | Alsobrook et al. | |
| 2007/0036783 A1 | 2/2007 | Humeau et al. | |
| 2007/0122378 A1 | 5/2007 | Freeman et al. | |
| 2009/0175867 A1 | 7/2009 | Thompson et al. | |
| 2009/0217401 A1 | 8/2009 | Korman et al. | |
| 2009/0258425 A1 | 10/2009 | Epstein et al. | |
| 2010/0028341 A1 | 2/2010 | Hermans et al. | |
| 2010/0081796 A1 | 4/2010 | Brinkman et al. | |
| 2010/0247521 A1 | 9/2010 | Jones et al. | |
| 2012/0100131 A1 | 4/2012 | Takayanagi et al. | |
| 2014/0044738 A1 | 2/2014 | Langermann et al. | |
| 2014/0242076 A1 | 8/2014 | Kadouche et al. | |

OTHER PUBLICATIONS

Anderson D.E. (2007) Expert Opin. Ther. Targets, 11(8): 1005-1009.*
Rieger et al., Glossary of Genetics pp. 11-12 (1991).
Yokosuka et al., "Programmed cell death 1 forms negative costimulatory microclusters that directly inhibit T cell receptor signaling by recruiting phosphatase SHP2", J Exp Med 209(6) 1201-1207 (2012).
Anderson "Chronic infection, T cell exhaustion, and breaking of tolerance," Role of Inflammation in Oncogenesis (2010) https://www.keystonesymposia.org/index.cfm?e=web.meeting.program&meetingid=1028.
Balaian et al., "Inhibition of acute myeloid leukemia cell growth by mono-specific and bi-specific anti-CD33 x anti-CD64 antibodies", Leukemia Research 28:821-829 (2004).
Chen et al., "Generation and Characterization of Four Novel Monoclonal Antibodies Against Human Programmed Death-1 Molecule", Hybridoma, 29: 153-160 (2010).
Chiba et al., "Tumor-infiltrating DCs suppress nucleic acid-mediated innate immune responses through interactions between the receptor TIM-3 and the alarmin HMGB1", Nat. Immunol, 13(9): 832-842 (2012).
Frank et al., "Early CD4+ T Cell Help Prevents Partial CD8+ T Cell Exhaustion and Promotes Maintenance of Herpes Simplex Virus 1 Latency", Journal of Immunology, 184(1): 277-286 (2010).
Golden-Mason et al., "Negative Immune Regulator Tim-3 Is Overexpressed on T Cells in Hepatitis C Virus Infection and Its Blockade Rescues Dysfunctional CD4+ and CD8+ T Cells", J. Virology, 83: 9122-9130 (2009).
Hafler et al., "TIMs: central regulators of immune responses", J. Exp. Med. 205: 2699-2701 (2008).
Nomi et al., "Clinical Significance and Therapeutic Potential of the Programmed Death-1 Ligand/Programmed Death-1 Pathway in Human Pancreatic Cancer", Clin. Cancer Res. 13(7): 2151-2157 (2007).
Riaz et al., "Strategies to enhance rituximab anti-tumor activity in the treatment of CD20-positive B-cell neoplasms", Immunologic Research, 46(1): 192-205 (2010).

(Continued)

*Primary Examiner* — Ilia I Ouspenski
(74) *Attorney, Agent, or Firm* — Nixon Peabody LLP; David S. Resnick; Mark J. FitzGerald

(57) ABSTRACT

Described herein are novel compositions comprising bispecific and multispecific polypeptide agents, and methods using these agents for targeting cells, such as functionally exhausted or unresponsive immune cells, that co-express the inhibitory receptors PD-1 and TIM-3. These compositions and methods are useful for the treatment of chronic immune conditions, such as persistent infections or cancer.

17 Claims, 13 Drawing Sheets

Specification includes a Sequence Listing.

(56) References Cited

OTHER PUBLICATIONS

Sakuishi et al. "OR.27 Tim-3/Tim-3L Pathway as a Target for Restoring E13ffector Functions in Exhausted CD8 Lymphocytes in Tumors", Clinical Immunology, (135): S12 Abstract (2010).

Sehrawat et al., "Galectin-9/TIM-3 Interaction Regulates Virus-Specific Primary and Memory CD8+ T Cell Response", PLoS Pathog, 6(5): e1000882 (2010).

Takamura et al., "Premature Terminal Exhaustion of Friend Virus-Specific Effector CD8+ T Cells by Rapid Induction of Multiple Inhibitory Receptors", J Immunol, 184(9): 4696-707 (2010).

Iwai et al., "Involvement of PD-L1 on tumor cells in the escape from host immune system and tumor immunotherapy by PD-L1 blockade", Proc Natl Acad Sci USA 99(19) 12293-12297 (2002).

Pilon-Thomas et al., "Blockade of Programmed Death Ligand 1 Enhances the Therapeutic Efficacy of Combination Immunotherapy against Melanoma", The Journal of Immunology 184(7) 3442-3449 (2010).

Hirano et al., "Blockade of B7-H1 and PD-1 by monoclonal antibodies potentiates cancer therapeutic immunity", Cancer Res 65(3) 1089-1096 (2005).

* cited by examiner

SEQUENCE LISTING

<160> NUMBER OF SEQ ID NOS: 4

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 301
<212> TYPE: PRT
<213> ORGANISM: Homo sapiens

<400> SEQUENCE: 2

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu

```
                   35                  40                  45
Val Pro Val Cys Trp Gly Lys Gly Ala Cys Pro Val Phe Glu Cys Gly
 50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Leu Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser
1               5

<210> SEQ ID NO 4
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: Sequence may encompass 1-8 repeating "Gly Gly
      Gly Gly Ser" units

<400> SEQUENCE: 4
```

```
Gly Gly Gly Gly Ser Gly Gly Gly Ser Gly Gly Gly Ser Gly
1               5               10              15
Gly Gly Gly Ser Gly Gly Gly Ser Gly Gly Gly Ser Gly Gly
            20              25              30
Gly Gly Ser Gly Gly Gly Ser
        35              40
```

BI-SPECIFIC ANTIBODIES AGAINST TIM-3 AND PD-1 FOR IMMUNOTHERAPY IN CHRONIC IMMUNE CONDITIONS

CROSS-REFERENCE TO RELATED APPLICATIONS

The application is a continuation application under 35 U.S.C. § 120 of a co-pending application U.S. Ser. No. 14/857,402 filed on Sep. 17, 2015, which is a continuation application under 35 U.S.C. § 120 of a application U.S. Ser. No. 13/805,030 filed on Mar. 5, 2013, and issued as U.S. Pat. No. 9,163,087, issued Oct. 20, 2015, which claims the benefit under 35 U.S.C. § 371 National Phase Entry Application of International Application No. PCT/US2011/040665 filed 16 Jun. 2011, which designates the U.S., and which claims benefit under 35 U.S.C. § 119(e) of U.S. Provisional Application Ser. No. 61/365,910 filed on Jul. 20, 2010 and U.S. Provisional Application Ser. No. 61/356,354 filed on Jun. 18, 2010, the contents of each of which are herein incorporated by reference in their entireties.

GOVERNMENT SUPPORT

This invention was made with Government Support under grants NIH P01AI073748 and NIH R01NS045937 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Nov. 2, 2017, is named 43214682.txt and is 6,348 bytes in size.

FIELD OF THE INVENTION

The invention relates to compositions and methods for targeting PD-1 and Tim-3 in the treatment of chronic immune conditions.

SUMMARY OF THE INVENTION

The inventors have discovered that the inhibitory receptor Tim-3 is expressed on CD8+ tumor-infiltrating lymphocytes (TILs) in mice bearing solid tumors, and that all Tim-3+ TILs co-express PD-1, another inhibitory receptor. Furthermore, the inventors have found that these Tim-3+ PD-1+ TILs represent the predominant fraction of CD8+ T cells infiltrating tumors. Also, the inventors have discovered that these Tim-3+ PD-1+ TILs show the greatest functional exhaustion, as measured by a failure to proliferate, and produce the cytokines IL-2, TNFα and IFNγ.

Accordingly, described herein are novel compositions comprising bispecific and multispecific polypeptide agents, and methods using these agents for targeting cells, such as functionally exhausted or unresponsive immune cells, that co-express the inhibitory receptors PD-1 and TIM-3. These compositions and methods are useful for the treatment of chronic immune conditions, such as persistent infections or cancer, where an immune response, such as an antigen-specific cytotoxic CD8 cell response, is inhibited or reduced due to the combined expression and activity of the PD-1 and TIM-3 inhibitory receptors. By blocking or inhibiting the interaction of these inhibitory receptors with their ligand, for example, by binding specifically to one or more ligand interaction sites, these compositions and methods prevent and/or inhibit PD-1 and TIM-3 inhibitory signals, and thus permit the restoration of or increase in the immune response.

In one aspect, described herein are multispecific polypeptide agents comprising at least one binding site that specifically binds to a PD-1 molecule, and at least one binding site that specifically binds to a TIM-3 molecule. In some embodiments of the aspect, the multispecific polypeptide agent is a multispecific antibody or a multispecific antibody fragment thereof.

In another aspect, described herein are bispecific polypeptide agents comprising a binding site that specifically binds to a PD-1 molecule, and a binding site that specifically binds to a TIM-3 molecule. In some embodiments of the aspect, the bispecific polypeptide agent is a bispecific antibody or a bispecific antibody fragment thereof.

In some embodiments of these aspects, and all such aspects described herein, the PD-1 molecule comprises the sequence set forth in SEQ ID NO:1, or is an allelic or splice variant of SEQ ID NO:1.

In some embodiments of these aspects, and all such aspects described herein, the TIM-3 molecule comprises the sequence set forth in SEQ ID NO:2, or is an allelic or splice variant of SEQ ID NO:2.

In some embodiments of these aspects, and all such aspects described herein, the binding site that specifically binds to the PD-1 molecule is directed against a PD-1 ligand interaction site. In some embodiments, specific binding to the PD-1 ligand interaction site modulates interaction of PD-1 with PD-L1. In some embodiments, specific binding to the PD-1 ligand interaction site modulates interaction of PD-1 with PD-L2. In some embodiments, specific binding to the PD-1 ligand interaction site modulates interaction of PD-1 with PD-L1 and PD-L2.

In some embodiments, the ligand interaction site of PD-1 comprises amino acid residues 41-136 of SEQ ID NO:1. In some embodiments, the ligand interaction site of PD-1 consists essentially of amino acid residues 41-136 of SEQ ID NO:1. In some embodiments, the ligand interaction site on PD-1 comprises any of the amino acid residues selected from the group consisting of amino acids 64, 66, 68, 73, 74, 75, 76, 78, 90, 122, 124, 126, 128, 130, 131, 132, 134, and 136 of SEQ ID NO:1. In some embodiments, the ligand interaction site on PD-1 comprises any of the amino acid residues selected from the group consisting of amino acids 78, 126, and 136 of SEQ ID NO:1.

In some embodiments of these aspects, and all such aspects described herein, the binding site that specifically binds to the TIM-3 molecule is directed against a TIM-3 ligand interaction site. In some embodiments, binding to the TIM-3 ligand interaction site modulates interaction of TIM-3 with galectin-9. In some embodiments, specific binding to the TIM-3 ligand interaction site modulates interaction of TIM-3 with phosphatidylserine. In some embodiments, specific binding to the TIM-3 ligand interaction site modulates interaction of TIM-3 with galectin-9 and phosphatidylserine.

In some embodiments, the TIM-3 ligand interaction site comprises amino acid residues 24-131 of SEQ ID NO:2. In some embodiments, the TIM-3 ligand interaction site consists essentially of amino acid residues 24-131 of SEQ ID NO:2. In some embodiments, the TIM-3 ligand interaction site comprises any of the amino acid residues selected from the group consisting of amino acids 50, 62, 69, 112, and 121 of SEQ ID NO:2. In some embodiments, the TIM-3 ligand interaction site comprises any of the amino acid residues selected from the group consisting of amino acids 44, 74, and 100 of SEQ ID NO:2.

Accordingly, in some aspects, described herein are pharmaceutical compositions comprising the multispecific or bispecific polypeptide agents comprising at least one binding site that specifically binds to a PD-1 molecule, and at least one binding site that specifically binds to a TIM-3 molecule as described herein, and a pharmaceutically acceptable carrier.

In some aspects, described herein are methods of treating subjects having chronic immune conditions. Such methods comprise administering to a subject having a chronic immune condition an effective amount of a multispecific polypeptide agent comprising at least one binding site that specifically binds to a PD-1 molecule, and at least one binding site that specifically binds to a TIM-3 molecule. In some embodiments, the multispecific polypeptide agent is a multispecific antibody or a multispecific antibody fragment thereof. Such methods can also comprise administering to a subject having a chronic immune condition an effective amount of a bispecific polypeptide agent comprising at least one binding site that specifically binds to a PD-1 molecule, and at least one binding site that specifically binds to a TIM-3 molecule. In some embodiments, the bispecific polypeptide agent is a bispecific antibody or a bispecific antibody fragment thereof. In some embodiments, the methods comprise activating an immune response in a subject having a chronic immune condition, by administering the multispecific and bispecific polypeptide agents described herein. In some embodiments, the methods further comprise the step of identifying or selecting a subject having a chronic immune condition, or a subject in need of an activated immune response.

In some embodiments of these methods, the PD-1 molecule comprises the sequence set forth in SEQ ID NO:1, or is an allelic or splice variant of SEQ ID NO:1. In some embodiments of these methods, and all such aspects described herein, the TIM-3 molecule comprises the sequence set forth in SEQ ID NO:2, or is an allelic or splice variant of SEQ ID NO:2.

In some embodiments of these methods, binding site that specifically binds to the PD-1 molecule is directed against a PD-1 ligand interaction site. In some embodiments, specific binding to the PD-1 ligand interaction site modulates interaction of PD-1 with PD-L1. In some embodiments, specific binding to the PD-1 ligand interaction site modulates interaction of PD-1 with PD-L2. In some embodiments, specific binding to the PD-1 ligand interaction site modulates interaction of PD-1 with PD-L1 and PD-L2.

In some embodiments, the ligand interaction site of PD-1 comprises amino acid residues 41-136 of SEQ ID NO:1. In some embodiments, the ligand interaction site of PD-1 consists essentially of amino acid residues 41-136 of SEQ ID NO:1. In some embodiments, the ligand interaction site on PD-1 comprises any of the amino acid residues selected from the group consisting of amino acids 64, 66, 68, 73, 74, 75, 76, 78, 90, 122, 124, 126, 128, 130, 131, 132, 134, and 136 of SEQ ID NO:1. In some embodiments, the ligand interaction site on PD-1 comprises any of the amino acid residues selected from the group consisting of amino acids 78, 126, and 136 of SEQ ID NO:1.

In some embodiments of these methods, the binding site that specifically binds to the TIM-3 molecule is directed against a TIM-3 ligand interaction site. In some embodiments, binding to the TIM-3 ligand interaction site modulates interaction of TIM-3 with galectin-9. In some embodiments, specific binding to the TIM-3 ligand interaction site modulates interaction of TIM-3 with phosphatidylserine. In some embodiments, specific binding to the TIM-3 ligand interaction site modulates interaction of TIM-3 with galectin-9 and phosphatidylserine.

In some embodiments, the TIM-3 ligand interaction site comprises amino acid residues 24-131 of SEQ ID NO:2. In some embodiments, the TIM-3 ligand interaction site consists essentially of amino acid residues 24-131 of SEQ ID NO:2. In some embodiments, the TIM-3 ligand interaction site comprises any of the amino acid residues selected from the group consisting of amino acids 50, 62, 69, 112, and 121 of SEQ ID NO:2. In some embodiments, the TIM-3 ligand interaction site comprises any of the amino acid residues selected from the group consisting of amino acids 44, 74, and 100 of SEQ ID NO:2.

In some embodiments of these methods, the chronic immune condition is a persistent infection. In some embodiments of these methods, the chronic immune condition is a cancer or a tumor. In some embodiments of these methods, the chronic immune condition comprises a population of functionally exhausted T cells. In some embodiments, the population of functionally exhausted T cells comprises a CD8+ T cell population. In some embodiments, the population of functionally exhausted T cells comprises a CD4+ T cell population. In some embodiments, the methods further comprise selecting a subject having a population of functionally exhausted T cells, such as a population of functionally exhausted CD8+ T cells, a population of functionally exhausted CD4+ T cells, or a combination thereof.

Definitions

As used herein, the term "bispecific polypeptide agent" refers to a polypeptide that comprises a first polypeptide domain which has a binding site that has binding specificity for a first target, and a second polypeptide domain which has a binding site that has binding specificity for a second target, i.e., the agent has specificity for two targets. The first target and the second target are not the same (i.e., are different targets (e.g., proteins)), but are both present (e.g., co-expressed) on a cell, such as on a cytotoxic T cell as described herein. A bispecific polypeptide agent described herein binds a cell that expresses both the first cell surface target and the second cell surface target more strongly (e.g., with greater avidity) than a cell that expresses only one target. Accordingly, a bispecific polypeptide agent as described herein can selectively and specifically bind to a cell that expresses the first target and the second target. A non-limiting example of a bispecific polypeptide agent is a bispecific antibody or antigen-binding fragment thereof.

As used herein, the term "multispecific polypeptide agent" refers to a polypeptide that comprises at least a first polypeptide domain having a binding site that has binding specificity for a first target, and a second polypeptide domain having a binding site that has binding specificity for a second target. The first target and the second target are not the same (i.e., are different targets (e.g., proteins)), but are both present (e.g., co-expressed) on a cell, such as on a cytotoxic T cell as described herein. A multispecific polypeptide agent as described herein can in addition bind one or more additional targets, i.e., a multispecific polypeptide can bind at least two, at least three, at least four, at least five, at least six, or more targets, wherein the multispecific polypeptide agent has at least two, at least, at least three, at least four, at least five, at least six, or more target binding sites respectively. A multispecific polypeptide agent binds a cell that expresses all the targets the agent is specific more strongly (e.g., with greater avidity) than a cell that expresses only one target, or less targets than the agent is specific for. A non-limiting example of a multispecific polypeptide agent is a multispecific antibody or antigen-binding fragment thereof. For the avoidance of doubt, a bispecific polypeptide agent is a type of multispecific polypeptide agent.

As used herein, the term "target" refers to a biological molecule (e.g., peptide, polypeptide, protein, lipid, carbohydrate) to which a polypeptide domain which has a binding site can selectively bind. The target can be, for example, an intracellular target (e.g., an intracellular protein target) or a cell surface target (e.g., a membrane protein, a receptor protein). Preferably, a target is a cell surface target, such as a cell surface protein. Preferably, the first cell surface target and second cell surface target are both present on a cell (e.g., a T cell).

The term "specificity" refers to the number of different types of antigens or antigenic determinants to which a particular antibody or antigen-binding fragment thereof can bind. The specificity of an antibody or antigen-binding fragment or portion thereof, alone or in the context of a bispecific or multispecific polypeptide agent, can be determined based on affinity and/or avidity. The affinity, represented by the equilibrium constant for the dissociation ($K_D$) of an antigen with an antigen-binding protein (such as a bispecific or multispecific polypeptide agent), is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$. As will be clear to the skilled person, affinity can be determined in a manner known per se, depending on the specific antigen of interest. Accordingly, a bispecific or multispecific polypeptide agent as defined herein is said to be "specific for" a first target or antigen compared to a second target or antigen when it binds to the first antigen with an affinity (as described above, and suitably expressed, for example as a $K_D$ value) that is at least 10 times, such as at least 100 times, and preferably at least 1000 times, and up to 10,000 times or more better than the affinity with which said amino acid sequence or polypeptide binds to another target or polypeptide. Preferably, when a bispecific or multispecific polypeptide agent is "specific for" a target or antigen compared to another target or antigen, it is directed against said target or antigen, but not directed against such other target or antigen.

Avidity is the measure of the strength of binding between an antigen-binding molecule (such as a bispecific polypeptide agent described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as a bispecific polypeptide agent described herein) will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. The $K_D$ for biological interactions which are considered meaningful (e.g. specific) are typically in the range of $10^{-10}$ M (0.1 nM) to $10^{-5}$ M (10000 nM). The stronger an interaction is, the lower is its $K_D$. Preferably, a binding site on a bispecific or multispecific polypeptide agent described herein will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of a polypeptide domain described herein to bind to a target, such as a molecule present on the cell-surface, with a $K_D 10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if a polypeptide agent described herein binds to TIM-3 with a $K_D$ of $10^{-5}$ M or lower, but not to TIM-1 or TIM-4, or a related homologue, then the agent is said to specifically bind TIM-3. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

As used herein, the term "double positive" refers to a cell that contains two different cell surface targets (different target species) that are bound by a polypeptide agent described herein. The polypeptide agents described herein bind double positive cells with high avidity. As used herein, the term "single positive" refers to a cell that contains only one cell surface target that is bound by a polypeptide agent, as described herein.

As used herein, "immunoglobulin" refers to a family of polypeptides which retain the immunoglobulin fold characteristic of antibody molecules, which comprise two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signaling (for example, receptor molecules, such as the PDGF receptor).

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on a polypeptide agent. Typically, antigens are bound by antibody ligands and are capable of raising an antibody response in vivo. An antigen can be a polypeptide, protein, nucleic acid or other molecule. Generally, the bispecific or multispecific polypeptide agents described herein are selected for target specificity against two particular antigens (i.e., PD-1 and TIM-3). In the case of conventional antibodies and fragments thereof, the antibody binding site as defined by the variable loops (L1, L2, L3 and H1, H2, H3) is capable of binding to the antigen. The term "antigenic determinant" refers to an epitope on the antigen recognized by an antigen-binding molecule (such as bispecific polypeptide agent described herein), and more particularly, by the antigen-binding site of said molecule.

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein.

An amino acid sequence (such as an antibody, a bispecific or multispecific polypeptide agent as described herein, or generally an antigen binding protein or polypeptide or a fragment thereof) that can specifically bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

With respect to a target or antigen, the term "ligand interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen, e.g., PD-1 and/or TIM-3. More generally, a "ligand interaction site" can be any site, epitope, antigenic determinant, part, domain or stretch of amino acid residues on a target or antigen to which a binding site of a bispecific or multispecific polypeptide agent described herein can bind such that the target or antigen (and/or any pathway, interaction, signalling, biological mechanism or biological effect in which the target or antigen is involved) is modulated.

As used herein, a "blocking" antibody or an antibody "antagonist" is one which inhibits or reduces biological activity of the antigen(s) it binds. For example, a PD-1 and TIM-3 bispecific antagonist antibody binds PD-1 and TIM-3 and inhibits the ability of PD-1 to, for example, bind PD-L1, and the inhibits the ability of TIM-3 to, for example, bind galectin-9. In certain embodiments, the blocking antibodies or antagonist antibodies or fragments thereof described herein completely inhibit the biological activity of the antigen(s).

"Universal framework" refers to a single antibody framework sequence corresponding to the regions of an antibody conserved in sequence as defined by Kabat ("Sequences of Proteins of Immunological Interest", US Department of Health and Human Services) or corresponding to the human germline immunoglobulin repertoire or structure as defined by Chothia and Lesk, *J. Mol. Biol.* 196: 910-917 (1987). The Kabat database is now also maintained on the world wide web. The compositions and methods described herein provide for the use of a single framework, or a set of such frameworks, which have been found to permit the derivation of virtually any binding specificity though variation in the hypervariable regions alone. The universal framework can be a $V_L$ framework ($V_\lambda$ or $V_\kappa$), such as a framework that comprises the framework amino acid sequences encoded by the human germline DPK1, DPK2, DPK3, DPK4, DPK5, DPK6, DPK7, DPK8, DPK9, DPK10, DPK12, DPK13, DPK15, DPK16, DPK18, DPK19, DPK20, DPK21, DPK22, DPK23, DPK24, DPK25, DPK26 or DPK 28 immunoglobulin gene segment. If desired, the $V_L$ framework can further comprise the framework amino acid sequence encoded by the human germline $J_\kappa 1$, $J_\kappa 2$, $J_\kappa 3$, $J_\kappa 4$, or $J_\kappa 5$ immunoglobulin gene segments. In other embodiments the universal framework can be a $V_H$ framework, such as a framework that comprises the framework amino acid sequences encoded by the human germline DP4, DP7, DP8, DP9, DP10, DP31, DP33, DP38, DP45, DP46, DP47, DP49, DP50, DP51, DP53, DP54, DP65, DP66, DP67, DP68 or DP69 immunoglobulin gene segments. If some embodiments, the $V_H$ framework can further comprise the framework amino acid sequence encoded by the human germline $J_H 1$, $J_H 2$, $J_H 3$, $J_H 4$, $J_H 4b$, $J_H 5$ and $J_H 6$ immunoglobulin gene segments.

As used herein "domain" refers to a folded protein structure which retains its tertiary structure independently of the rest of the protein. Generally, domains are responsible for discrete functional properties of proteins, and in many cases can be added, removed or transferred to other proteins without loss of function or properties of the remainder of the protein to which it is added or transferred and/or of the domain itself. In the context of an antibody, or an antibody fragment thereof, the term "binding domain" refers to such a domain that is directed against an antigenic determinant By "single antibody variable domain" is meant a folded polypeptide domain comprising sequences characteristic of antibody variable domains. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain. Thus, each polypeptide agent can comprise at least two different domains.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196: 901-917 (1987)). In some instances, a complementarity determining region can include amino acids from both a CDR region defined according to Kabat and a hypervariable loop. For example, the CDRH1 of the human heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

The "Fab" fragment contains a variable and constant domain of the light chain and a variable domain and the first constant domain ($C_H1$) of the heavy chain. $F(ab')_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90: 6444-6448 (1993).

The expression "linear antibodies" refers to the antibodies described in Zapata et al., *Protein Eng.*, 8(10): 1057-1062 (1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen Affinity matured antibodies are produced by procedures known in the art. Marks et al. Bio/Technology 10: 779-783 (1992) describes affinity maturation by $V_H$ and $V_L$ domain shuffling. Random mutagenesis of CDR and/or framework residues is described by: Barbas et al. Proc Nat. Acad. Sci, USA 91: 3809-3813 (1994); Schier et al. Gene 169: 147-155 (1995); Yelton et al. J. Immunol. 155: 1994-2004 (1995); Jackson et al., J. Immunol. 154(7): 3310-9 (1995); and Hawkins et al., J. Mol. Biol. 226: 889-896 (1992).

As used herein "complementary" refers to when two immunoglobulin domains belong to families of structures which form cognate pairs or groups or are derived from such families and retain this feature. For example, a $V_H$ domain and a $V_L$ domain of a natural antibody are complementary; two $V_H$ domains are not complementary, and two $V_L$ domains are not complementary. Complementary domains can be found in other members of the immunoglobulin superfamily, such as the $V_\alpha$ and $V_\beta$ (or γ and δ) domains of the T-cell receptor. Domains which are artificial, such as domains based on protein scaffolds which do not bind epitopes unless engineered to do so, are non-complementary. Likewise, two domains based on, for example, an immunoglobulin domain and a fibronectin domain are not complementary.

The process of designing/selecting and/or preparing a bispecific or multispecific polypeptide agent as described herein, is also referred to herein as "formatting" the amino acid sequence, and an amino acid sequence that is made part of a bispecific or multispecific polypeptide agent described herein is said to be "formatted" or to be "in the format of" that bispecific or multispecific polypeptide agent. Examples of ways in which an amino acid sequence can be formatted and examples of such formats will be clear to the skilled person based on the disclosure herein; and such formatted amino acid sequences form a further aspect of the bispecific or multispecific polypeptide agents described herein.

The term "library," as used herein, refers to a mixture of heterogeneous polypeptides or nucleic acids. The library is composed of members, each of which have a single polypeptide or nucleic acid sequence. To this extent, library is synonymous with repertoire. Sequence differences between library members are responsible for the diversity present in the library. The library can take the form of a simple mixture of polypeptides or nucleic acids, or can be in the form of organisms or cells, for example bacteria, viruses, animal or plant cells and the like, transformed with a library of nucleic acids. Preferably, each individual organism or cell contains only one or a limited number of library members. Advantageously, the nucleic acids are incorporated into expression vectors, in order to allow expression of the polypeptides encoded by the nucleic acids. In a preferred aspect, therefore, a library can take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

As used herein, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" can mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of a bispecific or multispecific polypeptide agent described herein.

As will be clear to the skilled person, "modulating" can also involve effecting a change (which can either be an increase or a decrease) in affinity, avidity, specificity and/or selectivity of a target or antigen for one or more of its ligands, binding partners, partners for association into a homomultimeric or heteromultimeric form, or substrates; and/or effecting a change (which can either be an increase or a decrease) in the sensitivity of the target or antigen for one or more conditions in the medium or surroundings in which the target or antigen is present (such as pH, ion strength, the presence of co-factors, etc.), compared to the same conditions but without the presence of a bispecific or multispecific polypeptide agent. Again, this can be determined in any suitable manner and/or using any suitable assay known per se, depending on the target or antigen involved.

"Modulating" can also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable (in vitro and usually cellular or in assay) assay known per se, depending on the target or antigen involved. In particular, an action as an agonist or antagonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the construct of a bispecific or multispecific polypeptide agent. By "reduce or inhibit" is meant the ability to cause an overall decrease preferably of 20% or greater, 30% or greater, 40% or greater, 45% or greater, more preferably of 50% or greater, of 55% or greater, of 60% or greater, of 65% or greater, of 70% or greater, and most preferably of 75%, 80%, 85%, 90%, 95%, or up to and including 100%.

Modulating can for example also involve allosteric modulation of the target or antigen; and/or reducing or inhibiting the binding of the target or antigen to one of its substrates or ligands and/or competing with a natural ligand, substrate for binding to the target or antigen. Modulating can also involve activating the target or antigen or the mechanism or pathway in which it is involved. Modulating can for example also involve effecting a change in respect of the folding or confirmation of the target or antigen, or in respect of the ability of the target or antigen to fold, to change its confirmation (for example, upon binding of a ligand), to associate with other (sub)units, or to disassociate. Modulating can for example also involve effecting a change in the ability of the target or antigen to transport other compounds or to serve as a channel for other compounds (such as ions).

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin®), anti-CD20 antibodies, an epidermal growth factor receptor (EGFR) antagonist (e.g., a tyrosine kinase inhibitor), HER1/EGFR inhibitor (e.g., erlotinib (Tarceva®)), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., .COPYRGT. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

By "reduce or inhibit" is meant the ability to cause an overall decrease preferably of 20% or greater, 30% or greater, 40% or greater, 45% or greater, more preferably of 50% or greater, of 55% or greater, of 60% or greater, of 65% or greater, of 70% or greater, and most preferably of 75% or greater, 80% or greater, 85% or greater, 90% or greater, or 95% or greater. Reduce or inhibit can refer to, for example, the symptoms of the disorder being treated, the presence or size of metastases or micrometastases, the size of the primary tumor, the presence or the size of the dormant tumor, or the load of infectious agent.

As used herein, the terms "functional exhaustion" or "unresponsiveness" refers to a state of a cell where the cell does not perform its usual function or activity in response to normal input signals. Such a function or activity includes, but is not limited to, proliferation or cell division, entrance into the cell cycle, cytokine production, cytotoxicity, or any combination thereof. Normal input signals can include, but are not limited to, stimulation via a receptor (e.g., T cell receptor, B cell receptor, co-stimulatory receptor). In particular embodiments of the aspects described herein, a cell that is functionally exhausted is a cytotoxic T lymphocyte (CTL) that expresses the CD8 cell surface marker. Such CTLs normally proliferate, lyse target cells (cytotoxicity), and/or produce cytokines such as IL-2, TNFα, IFNγ, or a combination therein in response to T cell receptor and/or co-stimulatory receptor stimulation. Thus, a functionally exhausted or unresponsive CTL or CD8+ T cell is one which does not proliferate, lyse target cells (cytotoxicity), and/or produce cytokines, such as IL-2, TNFα, IFNγ, in response to normal input signals. In other embodimens of the aspects described herein, a cell that is functionally exhausted is a helper T lymphocyte ($T_H$ cell) that expresses the CD4 cell surface marker. Such $T_H$ cells normally proliferate and/or produce cytokines such as IL-2, IFNγ, TNFα, IL-4, IL-5, IL-17, IL-10, or a combination thereof, in response to T cell receptor and/or co-stimulatory receptor stimulation. The cytokines produced by $T_H$ cells act, in part, to activate and/or otherwise modulate, i.e., "provide help," to other immune cells such as B cells and CD8+ cells. Thus, a functionally exhausted or unresponsive $T_H$ cell or CD4+ T cell is one which does not proliferate and/or produce cytokines, such as IL-2, IFNγ, TNFα, IL-4, IL-5, IL-17, IL-10 in response to normal input signals.

BRIEF DESCRIPTION OF THE FIGURES

FIG. 1A shows expression of Tim-3 and PD-1 on gated CD4+ and CD8+ TILs from a Balb/c mouse bearing CT26 tumor. FMO, fluorescence minus one controls for Tim-3 and PD-1 staining are shown. Data shown are representative of more than five independent analyses. FIG. 1B shows frequency of CD8+ cells in TILs expressing Tim-3 and PD-1 from tumor-bearing mice. *p<0.001, **p<0.05, one-way ANOVA followed by Tukey's multiple comparison test. CT26 (n=5), 4T1 (n=6), and B16 (n=9). FIG. 1C shows the frequency of CD8+ Tim-3+ cells in spleens of tumor-bearing mice compared to spleens of naïve tumor-free mice. *p<0.001, One-way ANOVA, Tukey's multiple comparison test and **p=0.0188, unpaired t-test. Balb/c (n=11), CT26 (n=8), 4T1 (n=7), C57BL/6 (n=5), B16 (n=10).

FIG. 2A shows representative staining on CD8+ Tim-3-PD-1-, Tim-3-PD-1+ and Tim-3+ PD-1+ TILs. FMO, fluorescence minus one controls for CD44 and CD62L staining are shown.Data are representative of 3 independent analyses. FIG. 2B depicts summary data showing the frequency of naïve ($CD44^{low}CD62L^{hi}$), Effector ($CD44^{low}CD62L^{low}$), Effector Memory ($CD44^{hi}CD62L^{low}$) and Central Memory ($CD44^{hi}CD62L^{hi}$) with the CD8+ Tim-3-PD-1+, and Tim-3+PD-1+ TILs. *p<0.05,**p<0.01,*p<0.001, One-way ANOVA, Tukey's multiple comparison test. N=3. Errors bars represent SEM.

FIG. 3A shows expression of cytokine in Tim-3-PD-1+ and Tim-3+ PD-1+ CD8+ TILs. Data shown are representative of five independent analyses. FMO, fluorescence minus one (anti-cytokine antibody). FIG. 3B shows frequency of Tim-3-PD-1+ and Tim-3+ PD-1+ cells among CD8+ cytokine producing and non-producing TILs (n=5). *p<0.0001,* *p=0.0261, unpaired t-test.

FIG. 4A shows expression of Ki-67 and TO-PRO-3 staining in CD8+ TILs showing the different phases of the cell cycle: G0, G1, and S→M. Data shown are representative of six independent analyses. FIG. 4B shows the ratio of Tim-3+ PD-1+ to Tim-3-PD-1+ TILs (n=6) in different phases of cell cycle. *p<0.05, One-way ANOVA, Tukey's multiple comparison test. N=6. Error bars represent SEM.

FIG. 5A shows that 5×10⁵ CT26 cells were implanted into wild type Balb/c mice. Mice were then treated with either anti-Tim-3, anti-PD-L1, anti-Tim-3+ anti-PD-L1, or control immunoglobulins (RatIgG1+ RatIgG2b). Error bars represent SEM. Two independent experiments are shown. Left panel, control (n=5), anti-Tim-3 (n=5), Anti-PD-L1 (n=6), anti-Tim-3+ anti-PD-L1 (n=5). Right panel, control (n=4), anti-Tim-3 (n=5), Anti-PD-L1 (n=4), anti-Tim-3+ anti-PD- L1 (n=3). FIG. 5B depicts the pooled data from the experiments shown in FIG. 5A. Left panel,*p<0.01 compared to control or Anti-Tim-3 group. Right panel, *p<0.01 compared to control group and p<0.05 compared to Anti-Tim-3 group. One-way ANOVA, Tukey's multiple comparison test.

DETAILED DESCRIPTION

Figure 1A:
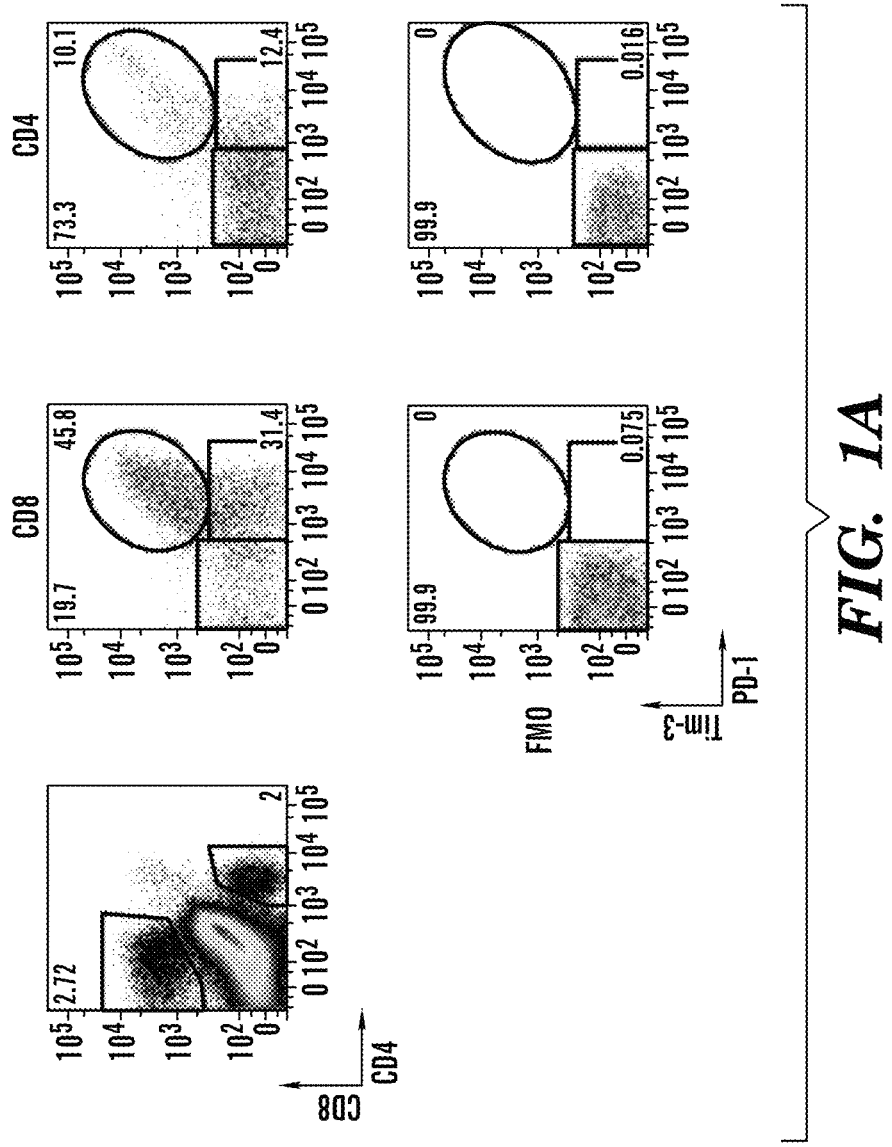
FIGS. 1A-1C show PD-1 and Tim-3 expression in tumor-infiltrating lymphocytes. Balb/c mice were implanted with CT26 colon adenocarcinoma or 4T1 mammary adenocarcinoma. C57BL/6 mice were implanted with B16F10 melanoma. TILs were harvested and stained with 7AAD, to exclude dead cells, and antibodies against CD8, CD4, Tim-3 and PD-1.

Described herein are compositions and methods for targeting cells co-expressing both the PD-1 and Tim-3 inhibitory receptors. These compositions and methods are based, in part, on the novel discovery that combined inhibition of the Tim-3 and PD-1 pathways restores immunological activities and functions of exhausted or unresponsive immune cells, such as T cells, and that such combined inhibition of these two pathways is more effective at controlling and treating chronic immune conditions characterized by a lack of or inhibition of a specific immune response, such as cancer or a persistent infection, than targeting either pathway alone.

Accordingly, described herein are novel compositions comprising bispecific and multispecific polypeptide agents that specifically bind to PD-1 and TIM-3 when these molecules are co-expressed on the surface of a cell, and methods for targeting cells, such as functionally exhausted or unresponsive immune cells, that co-express these inhibitory receptors, during chronic immune conditions. By blocking or inhibiting the interaction of these inhibitory receptors with their ligands, for example, by binding specifically to one or more ligand ineraction sites, these bispecific and multispecific polypeptide agents prevent and/or inhibit PD-1 and TIM-3 inhibitory signals, and thus permit the restoration of or increase the immune response of a cell expressing these receptors. Because these bispecific and multispecific polypeptide agents selectively bind cells that co-express PD-1 and TIM-3, undesirable effects that can result from delivering a therapeutic agent to a single positive cell can be avoided using the polypeptide agents described herein. For example, use of the bispecific and multispecific polypeptides in the compositions and methods described herein can prevent activation of non-exhausted or pathogenic, e.g., self-specific, T cells that express only Tim-3 or only PD-1, and prevent the unwanted targeting of effector cells expressing only Tim-3 or only PD-1 that are mounting a productive immune response.

PD-1 and PD-1 Ligands

PD-1 (or CD279) is a 288 amino acid type I transmembrane protein composed of one immunoglobulin (Ig) superfamily domain, a 20 amino acid stalk, a transmembrane domain, and an intracellular domain of approximately 95 residues containing an immunoreceptor tyrosine-based inhibitory motif (ITIM), as well as an immunoreceptor tyrosine-based switch motif (ITSM). PD-1 is encoded by the Pdcd1 and PDCD1 genes on chromosome 1 in mice and chromosome 2 in humans respectively. In both species, Pdcd1 consists of 5 exons. Exon 1 encodes a short signal sequence, whereas exon 2 encodes an Ig domain. The stalk and transmembrane domains make up exon 3, and exon 4 codes for a short 12 amino acid sequence that marks the beginning of the cytoplasmic domain. Exon 5 contains the C-terminal intracellular residues and a long 3' UTR (Keir M E et al., 2008. Annu Rev Immunol. 26: 677-704). PD-1 is a member of the B7 family of receptors.

Splice variants of PD-1 have been cloned from activated human T cells. These transcripts lack exon 2, exon 3, exons 2 and 3, or exons 2 through 4. All these variants, except for the splice variant lacking exon 3 only (PD-1Δex3), are expressed at similar levels as full-length PD-1 in resting peripheral blood mononuclear cells (PBMCs). All variants are significantly induced upon activation of human T cells with anti-CD3 and anti-CD28 (Keir M E et al., 2008. Annu Rev Immunol. 26: 677-704).

Accordingly, the term "PD-1" as used herein, refers to the 288 amino acid polypeptide having the amino acid sequence of: MQIPQAPWPVVWAVLQLGWRPGWFLDSPDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLC GAISLAPKAQIKESLRAELRVTERRAEVPTAHPSPSPRPAGQFQTLVVGVVGGLLGSLVLLVWVLAVICSRAARGTIGARRTGQPLKEDPSAVPVFSVDYGELDFQWREKTPEPPVPCVPEQTEYATIVFPSGMGTSSPARRGSADGPRSAQPLRPEDGHCSWPL (SEQ ID NO:1), as described by, e.g., NP_005009, together with any naturally occurring allelic, splice variants, and processed forms thereof. Typically, PD-1 refers to human PD-1. The term "PD-1" is also used to refer to truncated forms or fragments of the PD-1 polypeptide. Reference to any such forms of PD-1 can be identified in the application, e.g., by "PD-1 (42-136)." For example, the mature PD-1 peptide is referred to herein as PD-1(21-288), and PD-1 IgV domain as PD-1(42-136). Specific residues of PD-1 can be referred to as, for example, "PD-1(68)."

PD-1 has been shown to be expressed on T cells, B cells, natural killer T cells, activated monocytes, and dendritic cells (DCs). PD-1 is not expressed on resting T cells but is inducibly expressed after activation. Ligation of the T cell receptor or B cell receptor can upregulate PD-1 on T and B lymphocytes. In normal human reactive lymphoid tissue, PD-1 is expressed on germinal center-associated T cells. PD-1 compartmentalization in intracellular stores has been described in a regulatory T cell population. PD-1 is inducibly expressed on APCs on myeloid CD11c+ DCs and monocytes in humans (Keir M E et al., 2008. Annu Rev Immunol. 26: 677-704).

PD-1 has two known ligands, PD-L1 and PD-L2, which are also members of the B7 family. The binding interface of PD-1 to PD-L1 is via its IgV-like domain (i.e., PD-1(42-136)). Residues important for binding of PD-1 to its ligands include residues 64, 66, 68, 73, 74, 75, 76, 78, 90, 122, 124, 126, 128, 130, 131, 132, 134, and 136. PD-L1/CD274 has been shown to be constitutively expressed on mouse T and B cells, DCs, macrophages, mesenchymal stem cells, and bone marrow-derived mast cells. CD274/PD-L1 expression is also found on a wide range of nonhematopoietic cells and is upregulated on a number of cell types after activation. PD-L1 is expressed on almost all murine tumor cell lines, including PA1 myeloma, P815 mastocytoma, and B16 melanoma upon treatment with IFN-γ. Loss or inhibition of phosphatase and tensin homolog (PTEN), a cellular phosphatase that modifies phosphatidylinositol 3-kinase (PI3K) and Akt signaling, increases post-transcriptional PD-L1 expression in cancers (Keir M E et al., 2008. Annu Rev Immunol. 26: 677-704). Residues of PD-L1 important for binding to PD-1 include PD-L1(67), PD-L1(121), PD-L1(122), PD-L1(123), PD-L1(123), PD-L1(124), and PD-L1(126).

PD-L2 expression is more restricted than PD-L1 expression. PD-L2 is inducibly expressed on DCs, macrophages, and bone marrow-derived mast cells. PD-L2 is also expressed on 50% to 70% of resting peritoneal B1 cells, but not on conventional B2 B cells. PD-L2 can also be induced on monocytes and macrophages by GM-CSF, IL-4, and IFN-γ. PD-L2 expression has also been observed on tumor lines.

PD-1 and its ligands have been shown to have important roles in regulating immune defenses against microbes that cause acute and chronic infections. The PD-1:PD-L pathways appear to play important roles in the outcome of infection, and the regulation of the delicate balance between effective antimicrobial immune defenses and immune-mediated tissue damage. Accordingly, in some embodiments of the aspects described herein, a bispecific or multispecific polypeptide agent inhibits or blocks binding of PD-1 to its ligands.

A number of microorganisms that cause chronic infection appear to have exploited the PD-1:PD-L pathways to evade the immune responses and establish persistent infection. Studies in the lymphocytic choriomeningitis virus (LCMV) model of chronic viral infection were the first to show a role for the PD-1:PD-L pathway during chronic infection (Barber D L et al. 2006. Nature 439: 682-87). Viruses that cause chronic infections can render virus-specific T cells nonfunctional and thereby silence the antiviral T cell response (Wherry E J and Ahmed R. 2004. J. Virol. 78: 5535-45). Functional dysregulation, also termed herein as "exhaustion," of CD8 T cells is an important reason for ineffective viral control during chronic infections and is characteristic of chronic LCMV infection in mice, as well as of HIV, HBV, HCV, and HTLV infection in humans and SIV infection in primates.

In chronic viral infections in humans, several groups have shown that PD-1 expression is high on HIV-specific (Petrovas C et al. 2006. J. Exp. Med. 203: 2281-92; Day C L et al. 2006. Nature 443: 350-54; Trautmann L et al. 2006. Nat. Med. 12: 1198-202), HBV-specific (Boettler T et al. 2006. J. Virol. 80: 3532-40; Boni C et al. 2007. J. Virol. 81: 4215-25), and HCV-specific T cells (Bengsch B. et al., 2010 PLoS Pathog. 6(6); Urbani S et al. 2006. J. Virol. 80: 11398-403). Blocking PD-1:PD-L interactions in vitro has been shown to reverse the exhaustion of HIV-specific, HBV-specific (Boni C et al. 2007. J. Virol. 81: 4215-25), HCV-specific, and SIV-specific (Velu V et al. 2007. J. Virol. 81: 5819-28) CD8 and CD4 T cells and restores proliferation and cytokine production (Petrovas C et al. 2006. J. Exp. Med. 203: 2281-92; Day C L et al. 2006. Nature 443:350-54; Trautmann L et al. 2006. Nat. Med. 12: 1198-202; Urbani S et al. 2006. J. Virol. 80: 11398-403). Recent work shows that the HCV core, a nucleocapsid protein, can upregulate PD-1 and PD-L1 expression on healthy donor T cells and that upregulation of PD-1 is mediated by interaction of the HCV core with the complement receptor C1QBP (Yao Z Q et al. 2007. Viral Immunol. 20: 276-87).

The PD-1:PD-L pathway also can play a key role in the chronicity of bacterial infections. *Helicobacter pylori* causes chronic gastritis and gastroduodenal ulcers and is a risk factor for development of gastric cancer. During *H. pylori* infection, T cell responses are insufficient to clear infection, leading to persistent infection. Gastric epithelial cells express MHC class II molecules and are thought to have important APC (antigen-presenting cell) function during *H. pylori* infection. Anti-PD-L1 blocking antibodies enhance T cell proliferation and IL-2 production in cultures of gastric epithelial cells exposed to *H. pylori* and CD4 T cells, suggesting that the PD-1:PD-L1 pathway can play an important role in inhibiting T cell responses during *H. pylori* infection (Das S et al. 2006. J. Immunol. 176: 3000-9).

Parasitic worms also have exploited the PD-1:PD-L pathways to induce macrophages with strong suppressive function. During *Taenia crassiceps* infection in mice, a high percentage of CD4 T cells express PD-1, and PD-L1 and PD-L2 are upregulated on activated macrophages. Blockade of PD-L1, PD-L2, or PD-1 significantly decreased suppression of in vitro T cell proliferation by macrophages from *Taenia*-infected mice (Terrazas L I et al. 2005. Int. J. Parasitol. 35: 1349-58). Similarly, during *Schistosoma mansoni* infection in mice, macrophages express high levels of PD-L1 and more modest levels of PD-L2. Anti-PD-L1 completely abrogated the ability of these macrophages to suppress T cell proliferation in vitro, whereas anti-PD-L2 had no effect (Keir M E et al., 2008. Annu Rev Immunol. 26: 677-704).

The PD-1:PD-L pathways have also been shown to have distinct roles in the immune response to the protozoan parasite *Leishmania mexicana* (Keir M E et al., 2008. Annu Rev Immunol. 26: 677-704).

Tumors express antigens that can be recognized by host T cells, but immunologic clearance of tumors is rare. Part of this failure is due to immune suppression by the tumor microenvironment. Recent work has indicated that the PD-1: PD-L pathways are involved in suppression of anti-cancer/tumor immune responses. PD-1 expression is upregulated on tumor infiltrating lymphocytes, and this can contribute to tumor immunosuppression. PD-L1 expression has been shown in situ on a wide variety of solid tumors, including breast, lung, colon, ovarian, melanoma, bladder, liver, salivary, stomach, gliomas, thyroid, thymic epithelial, head, and neck. In addition, in ovarian cancer, PD-L1 expression is inversely correlated with intraepithelial, but not stromal, infiltrating CD8 T cells, suggesting that PD-L1 inhibits the intratumor migration of CD8 T cells. Also, studies relating PD-L1 expression on tumors to disease outcome show that PD-L1 expression strongly correlates with unfavorable prognosis in kidney, ovarian, bladder, breast, gastric, and pancreatic cancer but not small cell lung cancer (Keir M E et al., 2008. Annu Rev Immunol. 26: 677-704).

The PD-1 pathway can also play a role in hematologic malignancies. PD-1 is highly expressed on the T cells of angioimmunoblastic lymphomas, and PD-L1 is expressed on the associated follicular dendritic cell network. In nodular lymphocyte-predominant Hodgkin lymphoma, the T cells associated with lymphocytic and/or histiocytic (L&H) cells express PD-1. PD-1 and PD-L1 are expressed on CD4 T cells in HTLV-1-mediated adult T cell leukemia and lymphoma. PD-L2 has been identified as being highly expressed in mantle cell lymphomas. PD-L1 is expressed on multiple myeloma cells but not on normal plasma cells, and T cell expansion in response to myeloma cells is enhanced in vitro by PD-L1 blockade. PD-L1 is expressed on some primary T cell lymphomas, particularly anaplastic large cell T lymphomas (Keir M E et al., 2008. Annu Rev Immunol. 26: 677-704).

Accordingly, in some embodiments of the compositions and methods described herein, a bispecific or multispecific polypeptide agent inhibits or blocks binding of PD-1 to one or more of its ligands.

TIM-3 and TIM-3 Ligands

TIM-3 is a Type I cell-surface glycoprotein that comprises an N-terminal immunoglobulin (Ig)-like domain, a mucin domain with O-linked glycosylations and with N-linked glycosylations close to the membrane, a single transmembrane domain, and a cytoplasmic region with tyrosine phosphorylation motif(s). TIM-3 is a member of the T cell/transmembrane, immunoglobulin, and mucin (TIM) gene family.

Accordingly, the term "TIM-3" as used herein, refers to the 301 amino acid polypeptide having the amino acid sequence of: MFSHLPFDCVLLLLLLLLTRSSEVEY-RAEVGQNAYLPCFYTPAAPGNLVPVCWGKGACPVFE CGNVVLRTDERDVNYWTSRYWLNGDFRKGDVSL-TIENVTLADSGIYCCRIQIPGIMNDEKFN LKL-VIKPAKVTPAPTLQRDFTAAFPRMLTTRGHGP-PAETQTLGSLPDINLTQISTLANELRDSR LANDLRDSGATIRIGIYIGAGICAGLALALIFGAL-IFKWYSHSKEKIQNLSLISLANLPPSGLAN AVAEGIR-SEENIYTIEENVYEVEEPNEYYCYVSSRQQP-SQPLGCRFAMP (SEQ ID NO:2), as described by, e.g., AAL65157, together with any naturally occurring allelic, splice variants, and processed forms thereof. Typically, TIM-3 refers to human TIM-3. The term "TIM-3" is also used to refer to truncated forms or fragments of the TIM-3 polypeptide. Reference to any such forms or fragments of TIM-3 can be identified in the application, e.g., by "TIM-3 (24-131)." Specific residues of TIM-3 can be referred to as, for example, "TIM-3(62)."

TIM-3 was originally identified as a mouse Th1-specific cell surface protein that was expressed after several rounds of in vitro Th1 differentiation, and was later shown to also be expressed on Th17 cells. In humans, TIM-3 is expressed on a subset of activated CD4+ T cells, on differentiated Th1 cells, on some CD8+ T cells, and at lower levels on Th17 cells (Hastings W D, et al. 2009, Eur J Immunol. 39: 2492-2501). TIM-3 is also expressed on cells of the innate immune system including mouse mast cells, subpopulations of macrophages and dendritic cells (DCs), NK and NKT cells, and human monocytes, and on murine primary bronchial epithelial cell lines. TIM-3 expression is regulated by the transcription factor T-bet. TIM-3 can generate an inhibitory signal resulting in apoptosis of Th1 and Tc1 cells, and can mediate phagocytosis of apoptotic cells and cross-presentation of antigen. Polymorphisms in TIM-1 and TIM-3 can reciprocally regulate the direction of T-cell responses (Freeman G J et al., Immunol Rev. 2010 Can; 235(1): 172-89).

TIM-3 has two known ligands, galectin-9 and phosphatidylserine. Galectin-9 is an S-type lectin with two distinct carbohydrate recognition domains joined by a long flexible linker, and has an enhanced affinity for larger poly-N-acetyllactosamine-containing structures. Galectin-9 does not have a signal sequence and is localized in the cytoplasm. However, it can be secreted and exerts its function by binding to glycoproteins on the target cell surface via their carbohydrate chains (Freeman G J et al., Immunol Rev. 2010 Can; 235(1): 172-89).

Galectin-9 is expressed broadly including in immune cells and the epithelium of the gastrointestinal tract. Galectin-9 expression is particularly high in mast cells and also found in T cells, B cells, macrophages, endothelial cells, and fibroblasts. Galectin-9 production can be upregulated by IFN-γ. Galectin-9 has also been reported to exert various biologic functions via interaction with CD44 and IgE. Engagement of TIM-3 by galectin-9 leads to Th1 cell death and a consequent decline in IFN-γ production. When given in vivo, galectin-9 had beneficial effects in several murine disease models, including an EAE model, a mouse model of arthritis, in cardiac and skin allograft transplant models, and contact hypersensitivity and psoriatic models (Freeman G J et al., Immunol Rev. 2010 Can; 235(1): 172-89). Residues important for TIM-3 binding to galectin-9 include TIM-3 (44), TIM-3(74), and TIM-3(100), which undergo N- and/or O-glycosylation.

Both human and mouse TIM-3 have been shown to be receptors for phosphatidylserine (PtdSer), based on binding studies, mutagenesis, and a co-crystal structure, and it has been shown that TIM-3-expressing cells bound and/or engulfed apoptotic cells expressing PtdSer. Interaction of TIM-3 with PtdSer does not exclude an interaction with galectin-9 as the binding sites have been found to be on opposite sides of the IgV domain. Residues important for TIM-3 binding to PtdSer include TIM-3(50), TIM-3(62), TIM-3(69), TIM-3(112), and TIM-3(121).

Recent studies have implicated TIM-3 in mediating T-cell dysfunction associated with chronic viral infections (Golden-Mason L, et al., 2009 J Virol; 83: 9122-9130; Jones R B, et al., 2008 J Exp Med. 205: 2763-2779). In progressive HIV infection, it was found that TIM-3 was expressed on about 50% of CD8+ T cells, and was expressed on virus-specific CD8+ T cells. It was found that blocking of the TIM-3 pathway ex vivo increased HIV-1-specific T cell responses. Notably, it was found that the TIM-3+ T cell subset was primarily distinct from the PD-1+ T cell subset (Golden-Mason L, et al., 2009 J Virol; 83: 9122-9130).

In chronic HCV infection, TIM-3 expression was increased on CD4+ and CD8+ T cells, specifically HCV-specific CD8+ cytotoxic T cells (CTLs). It was found that a majority of virus-specific CTLs expressed PD-1, either alone, or co-expressed with Tim-3. Treatment with a blocking monoclonal antibody to TIM-3 reversed HCV-specific T cell exhaustion (Jones R B, et al., 2008 J Exp Med. 205: 2763-2779).

Accordingly, in some embodiments of the compositions and methods described herein, a bispecific or multispecific polypeptide agent inhibits or blocks binding of TIM-3 to one or more of its ligands.

Bispecific and Multispecific Polypeptide Agents for Targeting PD-1 and TIM-3

Described herein are bispecific and multispecific polypeptide agents that specifically bind to PD-1 and TIM-3 when these molecules are co-expressed on the surface of a cell, such as a functionally exhausted immune cell. The polypeptide agents can comprise at least one polypeptide domain having a binding site with binding specificity for a PD-1 target, and at least one polypeptide domain having a binding site with binding specificity for a TIM-3 target. As described herein, such polypeptide agents can selectively bind to double positive cells that co-express both PD-1 and TIM-3. Accordingly, polypeptides that specifically bind cell-surface antigens, such as antibodies and antigen-binding fragments thereof, can be formatted into polypeptide agents as described herein to provide agents that can selectively bind to cells that co-express PD-1 and TIM-3. Because these bispecific and multispecific polypeptide agents selectively bind cells that co-express PD-1 and TIM-3, undesirable effects that can result from delivering a therapeutic agent to a single positive cell (e.g., activation of non-exhausted or pathogenic (e.g., self-specific) T cells) can be avoided using the polypeptide agents described herein.

In some embodiments of the aspects described herein, a polypeptide agent can be formatted as a bispecific polypeptide agent as described herein, and in US 2010/0081796 and US 2010/0021473, the contents of which are herein incorporated in their entireties by reference. In other embodiments of the aspects described herein, a polypeptide agent can be formatted as a multispecific polypeptide agent, for example as described in WO 03/002609, the entire teachings of which are incorporated herein by reference.

Bispecific and multispecific polypeptide agents can comprise immunoglobulin variable domains that have different binding specificities. Such bispecific and multispecific polypeptide agents can comprise combinations of heavy and light chain domains. For example, a bispecific polypeptide agent can comprise a $V_H$ domain and a $V_L$ domain, which can be linked together in the form of an scFv (e.g., using a suitable linker such as Gly4Ser) that binds one target, i.e., either PD-1 or Tim-3. A construct that includes, e.g., an scFv that binds TIM-3 and an scFv that binds PD-1, is said to be bispecific for PD-1 and TIM-3. Similar arrangements can be applied in the context of, e.g., a bispecific $F(ab')_2$ construct.

Single domain antibody constructs are also contemplated for the development of bispecific reagents. In some embodiments of the aspects described herein, the bispecific and multispecific polypeptide agents may not comprise complementary $V_H/V_L$ pairs which form an antigen-binding site that binds to a single antigen or epitope co-operatively as found in conventional two chain antibodies. Instead, in some embodiments, the bispecific and multispecific polypeptide agents can comprise a $V_H/V_L$ complementary pair, wherein the V domains each have different binding specificities, such that two different epitopes or antigens are specifically bound.

In addition, in some embodiments, the bispecific and multispecific polypeptide agents comprise one or more $C_H$ or $C_L$ domains. A hinge region domain can also be included in some embodiments. Such combinations of domains can, for example, mimic natural antibodies, such as IgG or IgM, or fragments thereof, such as Fv, scFv, Fab or $F(ab')_2$ molecules. Other structures, such as a single arm of an IgG molecule comprising $V_H$, $V_L$, $C_H1$ and $C_L$ domains, are also encompassed within the embodiments described herein. Alternatively, in another embodiment, a plurality of bispecific polypeptide agents are combined to form a multimer. For example, two different bispecific polypeptide agents can be combined to create a tetra-specific molecule. It will be appreciated by one skilled in the art that the light and heavy variable regions of a bispecific or multispecific polypeptide agent produced according to the methods described herein can be on the same polypeptide chain, or alternatively, on different polypeptide chains. In the case where the variable regions are on different polypeptide chains, then they can be linked via a linker, generally a flexible linker (such as a polypeptide chain), a chemical linking group, or any other method known in the art.

In different embodiments of the aspects described herein, the bispecific and multispecific polypeptide agents can be formatted as bi- or multispecific antibodies or antigen-binding fragments thereof, or into bi- or multispecific non-antibody structures. Suitable formats include, for example, any suitable polypeptide structure in which an antibody variable domain, or one or more of the CDRs thereof, can be incorporated so as to confer binding specificity for antigen on the structure. A variety of suitable antibody formats are known in the art, such as, bispecific IgG-like formats (e.g., chimeric antibodies, humanized antibodies, human antibodies, single chain antibodies, heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a $F(ab')_2$ fragment), a single variable domain (e.g., $V_H$, $V_L$, $V_{HH}$), a dAb, and modified versions of any of the foregoing (e.g., modified by the covalent attachment of polyalkylene glycol (e.g., polyethylene glycol, polypropylene glycol, polybutylene glycol) or other suitable polymer).

A bispecific or multispecific polypeptide agent can be formatted using a suitable linker such as (Gly$_4$Ser)$_n$, where n=from 1 to 8, e.g., 2, 3, 4, 5, 6 or 7. If desired, bispecific or multispecific polypeptide agents can be linked to an antibody Fc region, comprising one or both of C$_H$2 and C$_H$3 domains, and optionally a hinge region. For example, vectors encoding bispecific or multispecific polypeptide agents linked as a single nucleotide sequence to an Fc region can be used to prepare such polypeptides.

In some embodiments of the aspects described herein, antigen-binding fragments of antibodies can be combined and/or formatted into non-antibody multispecific polypeptide structures to form multivalent complexes, which bind target molecules having the same epitope, thereby providing superior avidity. For example, natural bacterial receptors such as SpA can been used as scaffolds for the grafting of CDRs to generate ligands which bind specifically to one or more epitopes. Details of this procedure are described in U.S. Pat. No. 5,831,012, herein incorporated by reference in its entirety. Other suitable scaffolds include those based on fibronectin and affibodies. Details of suitable procedures are described in WO 98/58965, herein incorporated by reference in its entirety. Other suitable scaffolds include lipocallin and CTLA4, as described in van den Beuken et al., J. Mol. Biol. 310: 591-601 (2001), and scaffolds such as those described in WO 00/69907 (Medical Research Council), herein incorporated by reference in their entireties, which are based for example on the ring structure of bacterial GroEL or other chaperone polypeptides. In some embodiments, protein scaffolds can be combined. For example, CDRs specific for PD-1 and TIM-3 can be grafted onto a CTLA4 scaffold and used together with immunoglobulin V$_H$ or V$_L$ domains to form a bispecific or multispecific polypeptide agent. Likewise, fibronectin, lipocallin and other scaffolds can be combined in other embodiments.

In some embodiments of the aspects described herein, the bispecific or multispecific polypeptide agents can be formatted as fusion proteins that contain a first antigen-binding domain that is fused directly to a second antigen-binding domain. If desired, in some embodiments, such a format can further comprise a half-life extending moiety. For example, the bispecific or multispecific polypeptide agent can comprise a first antigen-binding domain specific for PD-1, that is fused directly to a second antigen-binding domain specific for TIM-3, that is fused directly to an antigen-binding domain that binds serum albumin.

Generally, the orientation of the polypeptide domains that have a binding site with binding specificity for a target, and whether a bispecific or multispecific polypeptide agent comprises a linker, are a matter of design choice. However, some orientations, with or without linkers, can provide better binding characteristics than other orientations. All orientations are encompassed by the aspects and embodiments described herein, and bispecific or multispecific polypeptide agents that contain an orientation that provides desired binding characteristics can be easily identified by screening.

Accordingly, in one aspect, described herein are multispecific agents comprising at least one binding site that specifically binds to a PD-1 molecule, and at least one binding site that specifically binds to a TIM-3 molecule. In one embodiment of this aspect, the PD-1 molecule bound by the multispecific agent has the sequence set forth in SEQ ID NO:1, or is an allelic or splice variant of SEQ ID NO:1. In one embodiment of this aspect, the TIM-3 molecule bound by the multispecific agent has the sequence set forth in SEQ ID NO:2, or is an allelic or splice variant of SEQ ID NO:2.

In one aspect, described herein are bispecific agents having a first binding site that specifically binds to a PD-1 molecule, and a second binding site that specifically binds to a TIM-3 molecule. In one embodiment of this aspect, the PD-1 molecule bound by the bispecific agent has the sequence set forth in SEQ ID NO:1, or is an allelic or splice variant of SEQ ID NO:1. In one embodiment of the aspect, the TIM-3 molecule bound by the bispecific agent has the sequence set forth in SEQ ID NO:2, or is an allelic or splice variant of SEQ ID NO:2.

It is to be understood that the bispecific or multispecific polypeptide agents described herein will generally bind to naturally occurring or synthetic analogs, variants, mutants, alleles, parts and fragments of a PD-1 and/or TIM-3 target; or at least to those analogs, variants, mutants, alleles, parts and fragments of a PD-1 and/or TIM-3 target, that contain one or more antigenic determinants or epitopes that are essentially the same as the antigenic determinant(s) or epitope(s) to which the bispecific or multispecific polypeptide agents described herein bind on the PD-1 and TIM-3 target. In some embodiments, the amino acid sequences and polypeptides described herein bind to some analogs, variants, mutants, alleles, parts and fragments of a PD-1 and/or TIM-3 target, but not to others.

In some embodiments of the aspects described herein, the binding sites of the bispecific polypeptide agents, such as the bispecific antibodies, are directed against a target's ligand interaction site. In other embodiments of the aspects described herein, the binding sites of the bispecific polypeptide agents are directed against a site on a target in the proximity of the ligand interaction site, in order to provide steric hindrance for the interaction of the target with its receptor or ligand. Preferably, the site against which the bispecific polypeptide agents described herein are directed is such that binding of the target to its receptor or ligand is modulated, and in particular, inhibited or prevented.

By binding to a PD-1 ligand interaction site, a bispecific polypeptide agent or multispecific polypeptide agent described herein can reduce or inhibit the activity or expression of PD-1. As used herein, a bispecific polypeptide agent or multispecific polypeptide agent that specifically binds to PD-1 has the ability to reduce the activity or expression of PD-1 in a cell (e.g., T cells such as CD8+ T cells) by at least 5%, at least 10%, at least 20%, at least 30%, at least 40%, at least 50%, at least 60%, at least 70%, at least 80%, at least 90%, at least 95% or up to and including 100% relative to untreated control levels.

By binding to a TIM-3 ligand interaction site, a bispecific polypeptide agent or multispecific polypeptide agent can reduce or inhibit the activity or expression of TIM-3. As used herein, a bispecific polypeptide agent or multispecific polypeptide agent that specifically binds to TIM-3 has the ability to reduce the activity or expression of TIM-3 in a cell (e.g., T cells such as CD8+ T cells) by at least 5%, at least 10%, at least 20%, at least 30%, at least 40%, at least 50%, at least 60%, at least 70%, at least 80%, at least 90%, at least 95%, or up to and including 100% relative to untreated control levels.

Thus, in some embodiments of the aspects described herein, a binding site of a bispecific or multispecific polypeptide agent is directed against a ligand interaction site on PD-1 such that the interaction of PD-1 with PD-L1 is modulated, and in particular inhibited or prevented. In other embodiments, a binding site of a bispecific or multispecific polypeptide agent is directed against a ligand interaction site on PD-1 such that the interaction of PD-1 with PD-L2 is modulated, and in particular inhibited or prevented. In other embodiments, a binding site of a bispecific or multispecific polypeptide agent is directed against a ligand interaction site on PD-1, such that the interaction of PD-1 with PD-L1 is modulated, and in particular inhibited or prevented, and a ligand interaction site such that the interaction of PD-1 with PD-L2 is modulated, and in particular inhibited or prevented. In other embodiments, a bispecific or multispecific polypeptide agent as described herein is directed against a ligand interaction site on PD-1 such that the interaction of PD-1 with PD-L1 is modulated, and in particular inhibited or prevented, while the interaction of PD-1 with PD-L2 is not modulated, inhibited, or prevented. In other embodiments, a bispecific or multispecific polypeptide agent as described herein is directed against a ligand interaction site on PD-1 such that the interaction of PD-1 with PD-L2 is modulated, and in particular inhibited or prevented while the interaction of PD-1 with PD-L1 is not modulated, inhibited or prevented.

Accordingly, in some embodiments of the aspects described herein, a ligand interaction site of PD-1 comprises amino acid residues 41-136 of SEQ ID NO:1. In some embodiments, a ligand interaction site on PD-1 comprises any of the amino acid residues selected from the group consisting of amino acids 64, 66, 68, 73, 74, 75, 76, 78, 90, 122, 124, 126, 128, 130, 131, 132, 134, and 136 of SEQ ID NO:1. In some embodiments, a ligand interaction site on PD-1 comprises any of the amino acid residues selected from the group consisting of amino acids 78, 126, and 136 of SEQ ID NO:1.

In some embodiments of the aspects described herein, a binding site of a bispecific or multispecific polypeptide agent is directed against a ligand interaction site on TIM-3 such that the interaction of TIM-3 with galectin-9 is modulated, and in particular inhibited or prevented. In other embodiments, a binding site of a bispecific or multispecific polypeptide agent is directed against a ligand interaction site on TIM-3 such that the interaction of TIM-3 with phosphatidylserine is modulated, and in particular inhibited or prevented. In other embodiments, a binding site of a bispecific or multispecific polypeptide agent is directed against a ligand interaction site on TIM-3, such that the interaction of TIM-3 with galectin-9 is modulated, and in particular inhibited or prevented, and a ligand interaction site such that the interaction of TIM-3 with phosphatidylserine is modulated, and in particular inhibited or prevented. In other embodiments, a bispecific or multispecific polypeptide agent as described herein is directed against a ligand interaction site on TIM-3 such that the interaction of TIM-3 with galectin-9 is modulated, and in particular inhibited or prevented, while the interaction of TIM-3 with phosphatidylserine is not modulated, inhibited, or prevented. In other embodiments, a bispecific or multispecific polypeptide agent as described herein is directed against a ligand interaction site on TIM-3 such that the interaction of TIM-3 with phosphatidylserine is modulated, and in particular inhibited or prevented while the interaction of TIM-3 with galectin-9 is not modulated, inhibited or prevented.

Accordingly, in some embodiments of the aspects described herein, a ligand interaction site of TIM-3 comprises amino acid residues 24-131 of SEQ ID NO:2. In some embodiments, a ligand interaction site on TIM-3 comprises any of the amino acid residues selected from the group consisting of amino acids 50, 62, 69, 112, and 121 of SEQ ID NO:2. In some embodiments, a ligand interaction site on PD-1 comprises any of the amino acid residues selected from the group consisting of amino acids 44, 74, and 100 of SEQ ID NO:2.

Antibodies suitable for practicing the methods described herein are preferably monoclonal and multispecific, and can include, but are not limited to, human, humanized or chimeric antibodies, comprising single chain antibodies, Fab fragments, F(ab') fragments, fragments produced by a Fab expression library, and/or binding fragments of any of the above. Antibodies also refer to immunoglobulin molecules and immunologically active portions of immunoglobulin molecules, i.e., molecules that contain at least two antigen or target binding sites that specifically bind PD-1 and TIM-3. The immunoglobulin molecules described herein can be of any type (e.g., IgG, IgE, IgM, IgD, IgA and IgY), class (e.g., IgG1, IgG2, IgG3, IgG4, IgA1 and IgA2) or subclass of immunoglobulin molecule, as is understood by one of skill in the art.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention may be made by the hybridoma method first described by Kohler et al., Nature 256: 495 (1975), or may be made by recombinant DNA methods (see, e.g., U.S. Pat. No. 4,816, 567). The "monoclonal antibodies" may also be isolated from phage antibody libraries using the techniques described in Clackson et al., Nature 352: 624-628 (1991) or Marks et al., J. Mol. Biol. 222: 581-597 (1991), for example.

The term "antibody fragment," as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) $F(ab')_2$ fragments, a bivalent fragment including two Fab' fragments linked by a disulphide bridge at the hinge region; (ix) single chain antibody molecules (e.g. single chain Fv; scFv) (Bird et al., Science 242: 423-426 (1988); and Huston et al., PNAS (USA) 85: 5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90: 6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10): 1057-1062 (1995); and U.S. Pat. No. 5,641,870).

In another aspect, bispecific antibodies having an IgG-like format are provided. Such formats have the conventional four chain structure of an IgG molecule (2 heavy chains and two light chains), in which one antigen-binding region (comprised of a $V_H$ and a $V_L$ domain) specifically binds PD-1 and the other antigen-binding region (also comprised of a $V_H$ and a $V_L$ domain) specifically binds TIM-3. In some embodiments, each of the variable regions (2 $V_H$ regions and 2 $V_L$ regions) is replaced with a dAb or single variable domain. The dAb(s) or single variable domain(s) that are included in an IgG-like format can have the same specificity or different specificities. In some embodiments, the IgG-like format is tetravalent and can have two, three or four specificities. For example, the IgG-like format can be bispecific and comprise 3 dAbs that have the same specificity and another dAb that has a different specificity; bispecific and comprise two dAbs that have the same specificity and two dAbs that have a common but different specificity; trispecific and comprise first and second dAbs that have the same specificity, a third dAb with a different specificity and a fourth dAb with a different specificity from the first, second and third dAbs; or tetraspecific and comprise four dAbs that each have a different specificity. Antigen-binding fragments of IgG-like formats (e.g., Fab, F(ab')$_2$, Fab', Fv, scFv) can be prepared as is known to one of skill in the art, and as described herein.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule is usually done by affinity chromatography steps, but the product yields are low. Similar procedures are disclosed in WO 93/08829, and in Traunecker et al, EMBO J., 10: 3655-3659 (1991), herein incorporated by reference in their entireties.

According to another approach, described in WO96/27011, herein incorporated by reference in its entirety, the interface between a pair of antibody molecules can be engineered to maximize the percentage of heterodimers which are recovered from recombinant cell culture. Such interfaces can comprise at least a part of the CH$_3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

In one aspect, the bispecific antibodies described herein include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies can be made using any convenient cross-linking methods. Suitable cross-linking agents are well known in the art, and are disclosed in U.S. Pat. No. 4,676,980, along with a number of cross-linking techniques. In one embodiment, the bispecific antibodies do not comprise a heteroconjugate.

Techniques for generating bispecific antibodies from antibody fragments have also been described in the literature. For example, bispecific antibodies can be prepared using chemical linkage. For example, Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. A bispecific antibody specific for PD-1 and TIM-3 produced using this method can be used in any of the compositions and methods described herein.

In some embodiments, a bispecific antibody specific for PD-1 and TIM-3 can be produced using any of the methods described in U.S. Patent Application No.: 20100233173; U.S. Patent Application No.: 20100105873; U.S. Patent Application No.: 20090155275; U.S. Patent Application No.: 20080071063; and U.S. Patent Application No.: 20060121042, the contents of each of which are herein incorporated in their entireties by reference. In some embodiments, a bispecific antibody specific for PD-1 and TIM-3 can be produced using any of the methods described in U.S. Patent Application No.: 20090175867 and U.S. Patent Application No.: 20110033483 the contents of which are herein incorporated in their entireties by reference.

In some embodiments, the bispecific antibodies can be made by the direct recovery of Fab'-SH fragments recombinantly expressed, e.g., in *E. coli*, and can be chemically coupled to form bispecific antibodies. For example, Shalaby et al., J Exp. Med, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Accordingly, this method can be used to generate a bispecific antibody to PD-1 and TIM-3 to restore responsiveness in immune cells, such as cytotoxic T cells.

Various techniques for making and isolating bispecific antibody fragments directly from recombinant cell culture have also been described, and can be used in the generation of the bispecific antibodies that specifically bind PD-1 and TIM-3. For example, bispecific antibodies have been produced using leucine zippers (Kostelny et al., J. Immunol, 148(5): 1547-1553 (1992)). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90: 6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_H$ and $V_L$ domains of another fragment, thereby forming two antigen-binding sites. Another strategy for making bispecific antibody fragments by the use of single-chain Fv (sFv) dimers has also been reported. See Gruber et al., J. Immunol., 152: 5368 (1994). Alternatively, the antibodies can be "linear antibodies" as described in Zapata et al. Protein Eng. 8(10): 1057-1062 (1995). Briefly, these antibodies comprise a pair of tandem Fd segments ($V_H$-$C_H$1-$V_H$-$C_H$1) which form a pair of antigen binding regions. Linear antibodies can be bispecific or multispecific.

Antibodies useful in the present methods can be described or specified in terms of the particular CDRs they comprise. The compositions and methods described herein encompass the use of an antibody or derivative thereof comprising a heavy or light chain variable domain, where the variable domain comprises (a) a set of three CDRs, and (b) a set of four framework regions, and in which the antibody or antibody derivative thereof specifically binds PD-1 and TIM-3.

Also provided herein are chimeric antibody derivatives of the bispecific and mutispecific polypeptide agents, i.e., antibody molecules in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81: 6851-6855 (1984)). Chimeric antibody molecules can include, for example, one or more antigen binding domains from an antibody of a mouse, rat, or other species, with human constant regions. A variety of approaches for making chimeric antibodies have been described and can be used to make chimeric antibodies containing the immunoglobulin variable region which recognizes the selected antigens, i.e., PD-1 and TIM-3, on the surface of differentiated cells or tumor-specific cells. See, for example, Takeda et al., 1985, Nature 314: 452; Cabilly et al., U.S. Pat. No. 4,816,567; Boss et al.; Tanaguchi et al., European Patent Publication EP171496; European Patent Publication 0173494, United Kingdom patent GB 2177096B).

The bispecific and mutispecific polypeptide agents described herein can also be a humanized antibody derivative. Humanized forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321: 522-525 (1986); Riechmann et al., Nature 332: 323-329 (1988); and Presta, Curr. Op. Struct. Biol. 2: 593-596 (1992).

Chemical conjugation can also be used to generate the bispecific or multispecific antibodies described herein, and is based on the use of homo- and heterobifunctional reagents with E-amino groups or hinge region thiol groups. Homobifunctional reagents such as 5,5'-Dithiobis(2-nitrobenzoic acid) (DNTB) generate disulfide bonds between the two Fabs, and 0-phenylenedimaleimide (O-PDM) generate thioether bonds between the two Fabs (Brenner et al., 1985, Glennie et al., 1987). Heterobifunctional reagents such as N-succinimidyl-3-(2-pyridylditio) propionate (SPDP) combine exposed amino groups of antibodies and Fab fragments, regardless of class or isotype (Van Dijk et al., 1989).

In some embodiments, the antibodies described herein, i.e., antibodies that are useful for treating chronic immune conditions and are specific for PD-1 and TIM-3, include derivatives that are modified, i.e., by the covalent attachment of any type of molecule to the antibody such that covalent attachment does not prevent the antibody from binding to PD-1 or TIM-3. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids.

Accordingly, the bispecific or multispecific antibodies described herein for use in the treatment of chronic immune conditions can be generated by any suitable method known in the art. Monoclonal and polyclonal antibodies against both PD-1 and TIM-3 are known in the art. To the extent necessary, e.g., to generate antibodies with particular characteristics or epitope specificity, the skilled artisan can generate new monoclonal or polyclonal anti-PD-1 and anti-TIM-3 antibodies as discussed below or as known in the art. In other embodiments, the bispecific and multispecific antibodies and antigen-binding fragments thereof described herein can utilize PD-1 binding site sequences from monoclonal antibodies against human PD-1, such as, MDX-1106 (ONO-4538), a fully human IgG4 anti-PD-1 blocking antibody (Journal of Clinical Oncology, 2008 Vol 26, No 15S); CT-011 (CureTech, LTD, previously CT-AcTibody or BAT), a humanized monoclonal IgG1 antibody (Benson D M et al., Blood. 2010 May 11), or those obtained from, clone NAT (Abcam), clone EH12.2H7 (Biolegend), clone J116 (eBioscience), clone MIH4 (eBioscience), clone J105 (eBioscience), or clone 192106 (R&D systems). Similarly, the bispecific and multispecific antibodies and antigen-binding fragments thereof described herein can utilize TIM-3 binding site sequences from monoclonal antibodies against human TIM-3, such as those obtained from, clone F38-2E2 (Biolegend), or clone 344823 (R&D Systems). For example, an antigen binding site against PD-1 having the amino acid sequences of the CDR regions of MDX-1106, and an antigen binding site against TIM-3 having the amino acid sequences of the CDR regions of the antibody produced by clone 344823 can be grafted onto an appropriate framework, such as a human IgG1 backbone, to generate a bispecific antibody construct as described herein.

Polyclonal antibodies specific for PD-1 or TIM-3 can be produced by various procedures well known in the art. For example, PD-1 or TIM-3 polypeptides or fragments thereof, such as a fragment comprising amino acid residues 42-136 of SEQ ID NO:1, or a fragment comprising amino acid residues 24-131 of SEQ ID NO:2, can be administered to various host animals including, but not limited to, rabbits, mice, rats, etc. to induce the production of sera containing polyclonal antibodies specific for the protein. Polyclonal antibodies are preferably raised in animals by multiple subcutaneous (sc) or intraperitoneal (ip) injections of the relevant antigen, e.g., a PD-1 fragment and an adjuvant. It can be useful to conjugate the antigen to a protein that is immunogenic in the species to be immunized, e.g., keyhole limpet hemocyanin, serum albumin, bovine thyroglobulin, or soy-bean trypsin inhibitor using a bifunctional or derivatizing agent, for example, maleimidobenzoyl sulfosuccinimide ester (conjugation through cysteine residues), N-hydroxy-succinimide (through lysine residues), glutaraldehyde, succinic anhydride, $SOCl_2$, or $R^1N{=}C{=}NR$, where R and $R^1$ are different alkyl groups.

Animals can be immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Various other adjuvants can be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Suitable adjuvants are also well known to one of skill in the art.

Monoclonal antibodies can be prepared using a wide variety of techniques known in the art including the use of hybridoma, recombinant, and phage display technologies, or a combination thereof. Various methods for making monoclonal antibodies described herein are available in the art. For example, the monoclonal antibodies can be made using the hybridoma method first described by Kohler et al., Nature, 256:495 (1975), or by recombinant DNA methods (U.S. Pat. No. 4,816,567). For example, monoclonal antibodies can be produced using hybridoma techniques including those known in the art and taught, for example, in Harlow et al., Antibodies: A Laboratory Manual, (Cold Spring Harbor Laboratory Press, 2nd ed., 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. It is to be understood that the term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with PD-1, TIM-3, or a fragment or derivative thereof, such as a fragment comprising amino acid residues 42-136 of SEQ ID NO:1, or a fragment comprising amino acid residues 24-131 of SEQ ID NO:2, or a cell expressing PD-1 or TIM-3, or a fragment thereof. Once an immune response is detected, e.g., antibodies specific for PD-1 or TIM-3 are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding PD-1 and TIM-3 and exerting a cytotoxic or cytostatic effect on activated lymphocytes. Ascites fluid, which generally contains high levels of antibodies, can be generated by injecting mice with positive hybridoma clones.

In the hybridoma method, a mouse or other appropriate host animal, such as a hamster or macaque monkey, is immunized as described above to elicit lymphocytes that produce or are capable of producing antibodies that will specifically bind to the protein used for immunization. Alternatively, lymphocytes can be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones can be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells can be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA can be placed into expression vectors, which are then transfected into host cells such as $E.$ $coli$ cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies is described in more detail below.

In another example, antibodies useful in the methods and compositions described herein can also be generated using various phage display methods known in the art, such as isolation from antibody phage libraries generated using the techniques described in McCafferty et al., Nature, 348: 552-554 (1990). Clackson et al., Nature, 352: 624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10: 779-783 (1992)), as well as combinatorial infection and in vivo recombination as a strategy for constructing very large phage libraries (Waterhouse et al., Nuc. Acids. Res., 21: 2265-2266 (1993)). Thus, these techniques are viable alternatives to traditional monoclonal antibody hybridoma techniques for isolation of monoclonal antibodies.

In phage display methods, functional antibody domains are displayed on the surface of phage particles which carry the nucleic acid sequences encoding them. In a particular embodiment, such phage can be utilized to display antigen binding domains expressed from a repertoire or combinatorial antibody library (e.g. human or murine). In phage display methods, functional antibody domains are displayed on the surface of phage particles which carry the nucleic acid sequences encoding them. In particular, DNA sequences encoding $V_H$ and $V_L$ domains are amplified from animal cDNA libraries (e.g., human or murine cDNA libraries of lymphoid tissues). The DNA encoding the $V_H$ and $V_L$ domains are recombined together with an scFv linker by PCR and cloned into a phagemid vector (e.g., p CANTAB 6 or pComb 3 HSS). The vector is electroporated into $E.$ $coli$ and the $E.$ $coli$ is infected with helper phage. Phage used in these methods are typically filamentous phage including fd and M13 binding domains expressed from phage with Fab, Fv or disulfide stabilized Fv antibody domains recombinantly fused to either the phage gene III or gene VIII protein. Phage expressing an antigen binding domain that binds to PD-1 or TIM-3 or portions thereof can be selected or identified with antigen e.g., using labeled antigen or antigen bound or captured to a solid surface or bead. Examples of phage display methods that can be used to make the antibodies described herein include those disclosed in Brinkman et al, 1995, J. Immunol. Methods 182: 41-50; Ames et al., 1995, J. Immunol. Methods 184: 177-186; Kettleborough et al, 1994, Eur. J. Immunol. 24: 952-958; Persic et al., 1997, Gene 187: 9-18; Burton et al., 1994, Advances in Immunology, 191-280; PCT Application No. PCT/GB91/01134; PCT Publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403, 484; 5,580,717; 5,427,908; 5,750,753; 5,821,047; 5,571, 698; 5,427,908; 5,516,637; 5,780,225; 5,658,727; 5,733,743 and 5,969,108, the contents of which are herein incorporated by reference in their entireties.

As is described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al, BioTechniques 1992, 12(6): 864-869; and Sawai et al, 1995, AJRI 34: 26-34; and Better et al., 1988, Science 240: 1041-1043, the contents of which are herein incorporated by reference in their entireties.

As used herein, a "chimeric antibody" refers to a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science, 1985, 229: 1202; Oi et al, 1986, BioTechniques 4: 214; Gillies et al., 1989, J. Immunol. Methods 125: 191-202; U.S. Pat. Nos. 5,807,715; 4,816,567; and 4,816,397, the contents of which are herein incorporated by reference in their entireties.

"Humanized antibodies," as the term is used herein, refer to antibody molecules from a non-human species, where the antibodies that bind the desired antigen, i.e., PD-1 or TIM-3, have one or more CDRs from the non-human species, and framework and constant regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., 1988, Nature 332: 323. Antibodies can be humanized using a variety of techniques known in the art including, for example, CDR-grafting (EP 239,400; PCT publication WO 91/09967; U.S. Pat. Nos. 5,225,539; 5,530,101; and 5,585, 089), veneering or resurfacing (EP 592,106; EP 519,596; Padlan, Molecular Immunology, 1991, 28(4/5): 489-498; Studnicka et al., 1994, Protein Engineering 7(6): 805-814; Roguska. et al, 1994, PNAS 91: 969-973), and chain shuffling (U.S. Pat. No. 5,565,332), the contents of which are herein incorporated by reference in their entireties. Accordingly, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321: 522-525 (1986); Riechmann et al., Nature, 332: 323-327 (1988); Verhoeyen et al., Science, 239: 1534-1536 (1988)), the contents of which are herein incorporated by reference in their entireties, by substituting rodent CDRs or CDR sequences for the corresponding sequences of a human antibody. Accordingly, such "humanized" antibodies are chimeric antibodies (U.S. Pat. No. 4,816,567, the contents of which are herein incorporated by reference in its entirety) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151: 2296 (1993); Chothia et al., J. Mol. Biol., 196: 901 (1987)). Another method uses a particular framework derived from the consensus sequence of all human antibodies of a particular subgroup of light or heavy chains. The same framework can be used for several different humanized antibodies (Carter et al., Proc. Natl. Acad. Sci. USA, 89: 4285 (1992); Presta et al., J. Immunol., 151: 2623 (1993)).

It is further important that antibodies be humanized with retention of high affinity for the antigen, i.e., PD-1 and TIM-3, and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding Humanized antibodies and affinity matured variants thereof directed against the VEgf antigen are described in, for example, U.S. Pat. No. 6,884,879 issued Feb. 26, 2005, the contents of which are herein incorporated by reference in its entirety.

Completely human antibodies are particularly desirable for the therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741, the contents of which are herein incorporated by reference in their entireties.

Human antibodies can also be produced using transgenic mice which express human immunoglobulin genes, and upon immunization are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. The transgenic mice are immunized in the normal fashion with a selected antigen, e.g., all or a portion of PD-1 and TIM-3. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, Lonberg and Huszar, 1995, Int. Rev. Immunol. 13: 65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661, 016; 5,545,806; 5,814,318; 5,885,793; 5,916,771; and 5,939,598, the contents of which are herein incorporated by reference in their entireties. In addition, companies such as Abgenix, Inc. (Freemont, Calif.) and Medarex (Princeton, N.J.) can be engaged to provide human antibodies directed against a selected antigen using technology similar to that described above. See also, e.g., Jakobovits et al., Proc. Natl. Acad. Sci. USA, 90: 2551 (1993); Jakobovits et al., Nature, 362: 255-258 (1993); Bruggermann et al., Year in Immuno., 7: 33 (1993); and Duchosal et al. Nature 355: 258 (1992), the contents of which are herein incorporated by reference in their entireties.

Alternatively, phage display technology (McCafferty et al., Nature 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S, and Chiswell, David J., Current Opinion in Structural Biology 3: 564-571 (1993). Several sources of V-gene segments can be used for phage display. Clackson et al., Nature, 352: 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222: 581-597 (1991), or Griffith et al., EMBO J. 12: 725-734 (1993). See, also, U.S. Pat. Nos. 5,565,332 and 5,573,905.

Human antibodies can also be generated by in vitro activated B cells (see U.S. Pat. Nos. 5,567,610 and 5,229,275, the contents of which are herein incorporated by reference in their entireties).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1994, Bio/technology 12: 899-903).

Further, the bispecific and multispecific antibodies to PD-1 or TIM-3 described herein can, in turn, be utilized to generate anti-idiotype antibodies that "mimic" proteins described herein using techniques well known to those skilled in the art. (See, e.g. Greenspan & Bona, 1989, FASEB J. 7(5): 437-444; and Nissinoff. 1991, J. Immunol. 147(8): 2429-2435). Fab fragments of such anti-idiotypes can be used in therapeutic regimens to elicit an individual's own immune response against PD-1 or TIM-3 present on activated lymphocytes.

Various techniques have been developed for the production of antibody fragments. The antibodies described herein can be fragmented using conventional techniques and the fragments screened for utility in the same manner as described above for the whole antibodies. Traditionally, these fragments were derived via proteolytic digestion of intact antibodies (see, e.g., Morimoto et al., Journal of Biochemical and Biophysical Methods 24: 107-117 (1992) and Brennan et al., Science, 229: 81 (1985)). For example, Fab and $F(ab')_2$ fragments of the bispecific and multispecific antibodies described herein can be produced by proteolytic cleavage of immunoglobulin molecules, using enzymes such as papain (to produce Fab fragments) or pepsin (to produce $F(ab')_2$ fragments). $F(ab')_2$ fragments contain the variable region, the light chain constant region and the $C_H1$ domain of the heavy chain. However, these fragments can now be produced directly by recombinant host cells. For example, the antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10: 163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

Examples of techniques which can be used to produce single-chain Fvs and antibodies include those described in U.S. Pat. Nos. 4,946,778 and 5,258,498; Huston et al., 1991, Methods in Enzymology 203: 46-88; Shu et al., 1993, PNAS 90: 7995-7999; and Skerra et al., 1988, Science 240: 1038-1040. For some uses, including the in vivo use of antibodies in humans as described herein and in vitro proliferation or cytotoxicity assays, it is preferable to use chimeric, humanized, or human antibodies.

In some embodiments, amino acid sequence modification(s) of the antibodies or antibody fragments described herein are contemplated. For example, it can be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics, e.g., specifically binds to PD-1 and TIM-3. The amino acid changes also can alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells Science, 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibodies with an N-terminal methionyl residue, or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated.

Substantial modifications in the biological properties of the antibodies or antibody fragments thereof described herein are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu;

(4) basic: His, Lys, Arg; (5) residues that influence chain orientation: Gly, Pro; (6) aromatic: Trp, Tyr, Phe. Non-conservative substitutions will entail exchanging a member of one of these classes for another class.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any cysteine residue not involved in maintaining the proper conformation of the antibody also can be substituted, generally with serine, to improve the oxidative stability of the molecule and prevent aberrant crosslinking. Conversely, cysteine bond(s) can be added to the antibody to improve its stability (particularly where the antibody is an antibody fragment such as an Fv fragment).

A particularly preferred type of substitutional variant involves substituting one or more hypervariable region residues of the parent antibody or antibody fragment thereof described herein (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it can be beneficial to analyze a crystal structure of the antigen-antibody complex to identify contact points between the antibody and human TIM-3 and PD-1. Such contact residues and neighboring residues are candidates for substitution according to the techniques elaborated herein. Once such variants are generated, the panel of variants is subjected to screening as described herein and antibodies with superior properties in one or more relevant assays can be selected for further development.

Another type of amino acid variant of the antibodies or antibody fragments thereof described herein alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used.

Addition of glycosylation sites to the antibodies or antibody fragments thereof described herein is conveniently accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody (for O-linked glycosylation sites).

Where the antibody or antibody fragment thereof described herein comprises an Fc region, the carbohydrate attached thereto can be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

It can be desirable to modify an antibody or antibody fragment thereof described herein with respect to effector function, e.g. so as to enhance antigen-dependent cell-mediated cyotoxicity (ADCC) and/or complement dependent cytotoxicity (CDC) of the antibody. This can be achieved by introducing one or more amino acid substitutions in an Fc region of the antibody or antibody fragment thereof. Alternatively or additionally, cysteine residue(s) can be introduced in the Fc region, thereby allowing interchain disulfide bond formation in this region. A homodimeric antibody thus generated can have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric antibodies with enhanced anti-tumor activity can also be prepared using heterobifunctional cross-linkers as described in Wolff et al. Cancer Research 53: 2560-2565 (1993). Alternatively, an antibody can be engineered which has dual Fc regions and can thereby have enhanced complement lysis and ADCC capabilities. See Stevenson et al. Anti-Cancer Drug Design 3: 219-230 (1989).

For example, WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody or antibody fragment thereof described herein, one can incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region can have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues). In one embodiment, the antibody has 307/434 mutations.

Nucleic acid molecules encoding amino acid sequence variants of the antibody or antibody fragment thereof described herein are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Methods of Treatment of Chronic Immune Conditions Using Bispecific and Multispecific Polypeptide Agents Targeting PD-1 and TIM-3

Certain aspects described herein are based, in part, on the discovery by the inventors that CD8+ T cells in a state of functional exhaustion, such as those found infiltrating a tumor site, co-express the inhibitory receptors PD-1 and TIM-3. The inventors found that TIM-3 expressing immune cells can further be sub-divided into TIM-3$^{lo}$ and TIM-3$^{hi}$ expressing cells. The inventors also found that the co-expression of PD-1 and TIM-3 on immune cells, such as CD8 T cells, can be restricted to or increased in a specific microenvironment, such as a tumor microenvironment, relative to other lymphoid tissue compartments. Further, the inventors found that the double-positive PD-1$^+$ TIM-3$^+$ cells have the greatest degree of functional impairment, i.e., least proliferation and cytokine production, when compared to single-positive CD8+ T cells expressing either only PD-1 or only TIM-3. In fact, the data described herein demonstrate that PD-1 alone is an imperfect marker of immune cell functional exhaustion, as it was found that PD-1 single positive (i.e., PD-1$^+$ TIM-3$^-$) CD8 cells infiltrating a tumor site included bonafide effector T cells that produced IFNγ, and were not functionally exhausted, and contained the highest frequency of IFNγ producing cells, even higher than the PD-1$^-$ TILs.

The inventors further discovered that combined targeting of the inhibitory receptors PD-1 and TIM-3 using, for example, antibodies specific for PD-1 and TIM-3, rescued and restored the function of exhausted CD8$^+$ T cells co-expressing these molecules, and thus restored anti-tumor immunity in vivo. In fact, it was found that mice in which both the TIM-3 and PD-1 pathways were targeted in a first tumor challenge remained tumor free even after a subsequent tumor re-challenge. These findings provide novel and specific cell-surface targeting of both PD-1 and TIM-3, by which to specifically target only those immune cells having a functionally unresponsive or exhausted phenotype and thus avoid generalized immune activation. Thus, the bispecific and multispecific polypeptide agents described herein, such as bispecific and multispecific antibodies and antibody fragments thereof, that can be used for co-targeting cells expressing both PD-1 and TIM-3, and methods using these agents, provide a novel means by which immune responses can be restored and/or initiated during chronic immune conditions characterized by functionally exhausted cells.

Accordingly, provided herein are methods for the treatment of chronic immune conditions, such as cancer and persistent infections, in a subject in need thereof. Some of these methods involve administering to a subject a therapeutically effective amount of one of the bispecific or multispecific polypeptide agents described herein. These methods are particularly aimed at therapeutic treatments of human subjects having a condition in which one or more immune cell populations, such as a CD8+ T cell population or a CD4+ T cell population, are functionally exhausted.

In one aspect, a method is provided for the treatment of a chronic immune condition in a subject in need thereof, comprising administering to a subject an effective amount of a multispecific polypeptide agent, wherein the multispecific polypeptide agent comprises at least one polypeptide domain that comprises a binding site that specifically binds to a PD-1 molecule, and at least one polypeptide domain that comprises a binding site that specifically binds to a TIM-3 molecule. In one embodiment, the multispecific polypeptide agent is a multispecific antibody or multispecific antibody-fragment thereof.

In one aspect, a method is provided for the treatment of a chronic immune condition in a subject in need thereof, comprising administering to a subject an effective amount of a bispecific polypeptide agent, wherein the bispecific polypeptide agent comprises one polypeptide domain that comprises a binding site that specifically binds to a PD-1 molecule, and one polypeptide domain that comprises a binding site that specifically binds to a TIM-3 molecule. In one embodiment, the bispecific polypeptide agent is a bispecific antibody or bispecific antibody-fragment thereof.

In some embodiments of these aspects, the PD-1 molecule has the sequence set forth in SEQ ID NO:1, or is an allelic or splice variant of SEQ ID NO:1. In other embodiments of these aspects, the TIM-3 molecule has the sequence set forth in SEQ ID NO:2, or is an allelic or splice variant of SEQ ID NO:2.

In some embodiments of the methods described herein, the binding sites of the multispecific and bispecific polypeptide agents are directed against a ligand interaction site. In other embodiments of the aspects described herein, the binding sites of the multispecific and bispecific polypeptide agents are directed against a site in the proximity of a ligand interaction site, such that the agent sterically hinders the interaction of the PD-1 or TIM-3 target with a ligand.

Thus, in some embodiments of the aspects described herein, the binding site of the bispecific or multispecific polypeptide agent being administered to the subject as described herein, is directed against the ligand interaction site on PD-1, such that the interaction of PD-1 with PD-L1 is modulated, and in particular inhibited or prevented. In other embodiments, the binding site of the bispecific or multispecific polypeptide agent is directed against the ligand interaction site on PD-1 such that the interaction of PD-1 with PD-L2 is modulated, and in particular inhibited or prevented. In other embodiments, the binding site of the bispecific or multispecific polypeptide agent is directed against both the ligand interaction site on PD-1, such that the interaction of PD-1 with PD-L1 is modulated, and in particular inhibited or prevented, and the ligand interaction site on PD-1 such that the interaction of PD-1 with PD-L2 is modulated, and in particular inhibited or prevented. In other embodiments, the bispecific or multispecific polypeptide agent being administered to the subject is directed against the ligand interaction site on PD-1 such that the interaction of PD-1 with PD-L1 is modulated, and in particular inhibited or prevented, while the interaction of PD-1 with PD-L2 is not modulated, inhibited, or prevented. In other embodiments, the bispecific or multispecific polypeptide agent is directed against the ligand interaction site on PD-1 such that the interaction of PD-1 with PD-L2 is modulated, and in particular inhibited or prevented, while the interaction of PD-1 with PD-L1 is not modulated, inhibited or prevented.

Accordingly, in some embodiments of the methods and compositions described herein, the ligand interaction site of PD-1 comprises amino acid residues 41-136 of SEQ ID NO:1. In some embodiments, the ligand interaction site on PD-1 comprises any of the amino acid residues selected from the group consisting of amino acids 64, 66, 68, 73, 74, 75, 76, 78, 90, 122, 124, 126, 128, 130, 131, 132, 134, and 136 of SEQ ID NO:1. In some embodiments, the ligand interaction site on PD-1 comprises any of the amino acid residues selected from the group consisting of amino acids 78, 126, and 136 of SEQ ID NO:1. In some embodiments, the ligand interaction site on PD-1 comprises the group consisting of amino acids 78, 126, and 136 of SEQ ID NO:1.

In some embodiments of the aspects described herein, the binding site of the bispecific or multispecific polypeptide agent being administered to the subject as described herein, is directed against the ligand interaction site on TIM-3 such that the interaction of TIM-3 with galectin-9 is modulated, and in particular inhibited or prevented. In other embodiments, the binding site of the bispecific and multispecific polypeptide agent is directed against the ligand interaction site on TIM-3 such that the interaction of TIM-3 with phosphatidylserine is modulated, and in particular inhibited or prevented. In other embodiments, the binding site of the bispecific and multispecific polypeptide agent is directed against both the ligand interaction sites on TIM-3, such that the interaction of TIM-3 with galectin-9 is modulated, and in particular inhibited or prevented, and the interaction of TIM-3 with phosphatidylserine is modulated, and in particular inhibited or prevented. In other embodiments, the binding site of the bispecific and multispecific polypeptide agent as described herein is directed against the ligand interaction site on TIM-3 such that the interaction of TIM-3 with galectin-9 is modulated, and in particular inhibited or prevented, while the interaction of TIM-3 with phosphatidylserine is not modulated, inhibited, or prevented. In other embodiments, the binding site of the bispecific and multi-specific polypeptide agent is directed against the ligand interaction site on TIM-3 such that the interaction of TIM-3 with phosphatidylserine is modulated, and in particular inhibited or prevented, while the interaction of TIM-3 with galectin-9 is not modulated, inhibited, or prevented.

In some embodiments of the methods and compositions described herein, the ligand interaction site of TIM-3 comprises amino acid residues 24-131 of SEQ ID NO:2. In some embodiments, the ligand interaction site on TIM-3 comprises any of the amino acid residues selected from the group consisting of amino acids 50, 62, 69, 112, and 121 of SEQ ID NO:2. In some embodiments, a ligand interaction site on PD-1 comprises any of the amino acid residues selected from the group consisting of amino acids 44, 74, and 100 of SEQ ID NO:2.

The terms "subject" and "individual" are used interchangeably herein, and refer to an animal, for example a human, recipient of the bispecific or multispecific polypeptide agents described herein. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject.

Modes of Administration

The bispecific or multispecific polypeptide agents described herein can be administered to a subject in need thereof by any appropriate route which results in an effective treatment in the subject. As used herein, the terms "administering," and "introducing" are used interchangeably and refer to the placement of a bispecific or multispecific polypeptide agent into a subject by a method or route which results in at least partial localization of such agents at a desired site, such as a site of inflammation, such that a desired effect(s) is produced.

In some embodiments, the bispecific or multispecific polypeptide agent is administered to a subject having a chronic immune condition by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the bispecific or multispecific polypeptide agents for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the bispecific or multispecific polypeptide agent other than directly into a target site, tissue, or organ, such as a tumor site, such that it enters the subject's circulatory system and, thus, is subject to metabolism and other like processes.

For the clinical use of the methods described herein, administration of the bispecific or multispecific polypeptide agents can include formulation into pharmaceutical compositions or pharmaceutical formulations for parenteral administration, e.g., intravenous; mucosal, e.g., intranasal; ocular, or other mode of administration. In some embodiments, the bispecific or multispecific polypeptide agents described herein can be administered along with any pharmaceutically acceptable carrier compound, material, or composition which results in an effective treatment in the subject. Thus, a pharmaceutical formulation for use in the methods described herein can contain a bispecific or multispecific polypeptide agent as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, a bispecific or multispecific polypeptide agent. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alchols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The bispecific or multispecific polypeptide agents described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a bispecific or multispecific polypeptide agent can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Further embodiments of the formulations and modes of administration of the bispecific or multispecific polypeptide agents that can be used in the methods described herein are illustrated below.

Parenteral Dosage Forms. Parenteral dosage forms of the bispecific or multispecific polypeptide agents can also be administered to a subject with a chronic immune condition by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol Formulations.

A bispecific or multispecific polypeptide agent can be packaged in a pressurized aerosol container together with suitable propellants, for example, hydrocarbon propellants like propane, butane, or isobutane with conventional adjuvants. A bispecific or multispecific polypeptide agent can also be administered in a non-pressurized form such as in a nebulizer or atomizer. A bispecific or multispecific polypeptide agent can also be administered directly to the airways in the form of a dry powder, for example, by use of an inhaler.

Suitable powder compositions include, by way of illustration, powdered preparations of a bispecific or multispecific polypeptide agent thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6: 273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8: 179-196 (1992)); Timsina et. al., Int. J. Pharm., 101: 1-13

(1995); and Tansey, I. P., Spray Technol. Market, 4: 26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the bispecific or multispecific polypeptide agents described herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms.

In some embodiments of the aspects described herein, a bispecific or multispecific polypeptide agent can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the bispecific or multispecific polypeptide agents described herein. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

In some embodiments, a bispecific or multispecific polypeptide agent for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of a bispecific or multispecific polypeptide agent administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Chronic Immune Conditions

Certain aspects of the methods described herein are based, in part, on the discovery by the inventors that co-targeting of the inhibitory receptors PD-1 and TIM-3 that are co-expressed by CD8+ T cells in a state of functional exhaustion, such as those found infiltrating a tumor site, can reverse the state of functional exhaustion and result in an effective immune response. Accordingly, the methods using the bispecific and multispecific polypeptide agents described herein are useful in the treatment of subjects having a chronic immune condition, such as a persistent infection or cancer, where an immune response is suppressed, insufficient, inhibited, or abrogated, due to functional exhaustion of a population of immune cells, such as CD8+ T cells. These methods provide specific targeting of cells to be activated, i.e, only those cells co-expressing both TIM-3 and PD-1, and prevent the unwanted or undesired activation of single-positive cells, cells that are not functionally exhausted, and cells that are pathogenic upon activation, e.g., self-reactive cells.

Immunosuppression of a host immune response plays a role in a variety of chronic immune conditions, such as in persistent infection and tumor immunosuppression. Recent evidence indicates that this immunosuppression can be mediated by immune inhibitory receptors expressed on the surface of an immune cell, and their interactions with their ligands. For example, cytotoxic CD8 T cells can enter a state of "functional exhaustion," or "unresponsiveness" whereby they express inhibitory receptors that prevent antigen-specific responses, such as proliferation and cytokine production. Accordingly, by inhibiting the activity and/or expression of such inhibitory receptors, an immune response to a persistent infection or to a cancer or tumor that is suppressed, inhibited, or unresponsive, can be enhanced or uninhibited.

As used herein, an "immune response" refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response.

As used herein, "unresponsiveness" or "functional exhaustion" with regard to immune cells includes refractivity of immune cells to stimulation, such as stimulation via an activating receptor or a cytokine. Unresponsiveness can occur, for example, because of exposure to immunosuppressants, exposure to high or constant doses of antigen, or through the activity of inhibitor receptors, such as PD-1 or TIM-3. As used herein, the term "unresponsiveness" includes refractivity to activating receptor-mediated stimulation. Such refractivity is generally antigen-specific and persists after exposure to the antigen has ceased. Unresponsive immune cells can have a reduction of at least 10%, 20%, 30%, 40%, 50%, 60%, 70%, 80%, 90%, 95%, or even 100% in cytotoxic activity, cytokine production, proliferation, trafficking, phagocytotic activity, or any combination thereof, relative to a corresponding control immune cell of the same type.

In some embodiments of the methods described herein, the subject being administered the bispecific or multispecific polypeptide agent that is specific for PD-1 and TIM-3 has a persistent infection with a bacterium, virus, fungus, or parasite. "Persistent infections" refer to those infections that, in contrast to acute infections, are not effectively cleared by the induction of a host immune response. During such persistent infections, the infectious agent and the immune response reach equilibrium such that the infected subject remains infectious over a long period of time without necessarily expressing symptoms. Persistent infections often involve stages of both silent and productive infection without rapidly killing or even producing excessive damage of the host cells. Persistent infections include for example, latent, chronic and slow infections. Persistent infection occurs with viruses including, but not limited to, human T-Cell leukemia viruses, Epstein-Barr virus, cytomegalovirus, herpesviruses, varicella-zoster virus, measles, papovaviruses, prions, hepatitis viruses, adenoviruses, parvoviruses and papillomaviruses.

In a "chronic infection," the infectious agent can be detected in the subject at all times. However, the signs and symptoms of the disease can be present or absent for an extended period of time. Non-limiting examples of chronic infection include hepatitis B (caused by heptatitis B virus (HBV)) and hepatitis C (caused by hepatitis C virus (HCV)) adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus JC, measles virus, rubella virus, human immunodeficiency virus (HIV), human T cell leukemia virus I, and human T cell leukemia virus II. Parasitic persistent infections can arise as a result of infection by, for example, *Leishmania, Toxoplasma, Trypanosoma, Plasmodium, Schistosoma,* and *Encephalitozoon.*

In a "latent infection," the infectious agent (such as a virus) is seemingly inactive and dormant such that the subject does not always exhibit signs or symptoms. In a latent viral infection, the virus remains in equilibrium with the host for long periods of time before symptoms again appear; however, the actual viruses cannot typically be detected until reactivation of the disease occurs. Non-limiting examples of latent infections include infections caused by herpes simplex virus (HSV)-1 (fever blisters), HSV-2 (genital herpes), and varicella zoster virus VZV (chickenpox-shingles).

In a "slow infection," the infectious agents gradually increase in number over a very long period of time during which no significant signs or symptoms are observed. Non-limiting examples of slow infections include AIDS (caused by HIV-1 and HIV-2), lentiviruses that cause tumors in animals, and prions.

In addition, persistent infections that can be treated using the methods described herein include those infections that often arise as late complications of acute infections. For example, subacute sclerosing panencephalitis (SSPE) can occur following an acute measles infection or regressive encephalitis can occur as a result of a rubella infection.

The mechanisms by which persistent infections are maintained can involve modulation of virus and cellular gene expression and modification of the host immune response. Reactivation of a latent infection can be triggered by various stimuli, including changes in cell physiology, superinfection by another virus, and physical stress or trauma. Host immunosuppression is often associated with reactivation of a number of persistent virus infections.

Additional examples of infectious viruses include: *Retroviridae; Picornaviridae* (for example, polio viruses, hepatitis A virus; enteroviruses, human coxsackie viruses, rhinoviruses, echoviruses); *Calciviridae* (such as strains that cause gastroenteritis); *Togaviridae* (for example, equine encephalitis viruses, rubella viruses); *Flaviridae* (for example, dengue viruses, encephalitis viruses, yellow fever viruses); *Coronaviridae* (for example, coronaviruses); *Rhabdoviridae* (for example, vesicular stomatitis viruses, rabies viruses); *Filoviridae* (for example, ebola viruses); *Paramyxoviridae* (for example, parainfluenza viruses, mumps virus, measles virus, respiratory syncytial virus); *Orthomyxoviridae* (for example, influenza viruses); *Bungaviridae* (for example, Hantaan viruses, bunga viruses, phleboviruses and Nairo viruses); *Arena viridae* (hemorrhagic fever viruses); *Reoviridae* (e.g., reoviruses, orbiviurses and rotaviruses); *Birnaviridae; Hepadnaviridae* (Hepatitis B virus); *Parvoviridae* (parvoviruses); *Papovaviridae* (papilloma viruses, polyoma viruses); *Adenoviridae* (most adenoviruses); *Herpesviridae* (herpes simplex virus (HSV) 1 and HSV-2, varicella zoster virus, cytomegalovirus (CMV), herpes viruses); *Poxviridae* (variola viruses, vaccinia viruses, pox viruses); and *Iridoviridae* (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Examples of fungal infections include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. The compositions and methods described herein are contemplated for use in treating infections with these fungal agents.

Examples of infectious bacteria include: *Helicobacterpyloris, Borelia burgdorferi, Legionella pneumophilia, Mycobacteria* sps (such as *M tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracia, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces Israelli*. The compositions and methods described herein are contemplated for use in treating infections with these bacterial agents. Other infectious organisms (such as protists) include: *Plasmodium falciparum* and *Toxoplasma gondii*. The compositions and methods described herein are contemplated for use in treating infections with these agents.

In some embodiments of the aspects described herein, the methods further comprise administering an effective amount of a viral, bacterial, fungal, or parasitic antigen in conjunction with the bispecific or multispecific polypeptide agent that specifically binds PD-1 and TIM-3. Non-limiting examples of suitable viral antigens include: influenza HA, NA, M, NP and NS antigens; HIV p24, pol, gp41 and gp120; Metapneumovirus (hMNV) F and G proteins; Hepatitis C virus (HCV) E1, E2 and core proteins; Dengue virus (DEN1-4) E1, E2 and core proteins; Human Papilloma Virus L1 protein; Epstein Barr Virus gp2201350 and EBNA-3A peptide; Cytomegalovirus (CMV) gB glycoprotein, gH glycoprotein, pp65, IE1 (exon 4) and pp 150; Varicella Zoster virus (VZV) IE62 peptide and glycoprotein E epitopes; Herpes Simplex Virus Glycoprotein D epitopes, among many others. The antigenic polypeptides can correspond to polypeptides of naturally occurring animal or human viral isolates, or can be engineered to incorporate one or more amino acid substitutions as compared to a natural (pathogenic or non-pathogenic) isolate.

In other embodiments of the methods described herein, the subject having a chronic immune condition being administered the bispecific or multispecific polypeptide agent that specifically binds PD-1 and TIM-3 has a cancer or tumor.

Studies have shown defective or supresssed immune responses in patients diagnosed with cancer. Described herein is the novel finding that tumor cells can co-express the ligands for the inhibitory ligands PD-1 and TIM-3, such that tumor infiltrating T cells expressing PD-1 and TIM-3 are in a state of functional exhaustion or unresponsiveness due to the inhibitory signals mediated by these receptors. Furthermore, described herein is the novel finding that targeting both the PD-1 and TIM-3 inhibitory pathways, using, for example, the bispecific or multispecific polypeptide agents described herein, restores or promotes the responsiveness of these T cells, such that a cancer or tumor is inhibited or reduced.

Accordingly, provided herein are methods to treat a subject having a cancer or tumor comprising administering an effective amount of a bispecific or multispecific polypeptide agent that is specific for PD-1 and TIM-3.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments described herein, the methods further comprise admininstering a tumor or cancer antigen to a subject being administered the bispecific or multispecific polypeptide agent that is specific for PD-1 and TIM-3 decribed herein.

A number of tumor antigens have been identified that are associated with specific cancers. As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER-2, mucins (i.e., MUC-1), prostate-specific antigen (PSA), and prostatic acid phosphatase (PAP). In addition, viral proteins such as hepatitis B (HBV), Epstein-Barr (EBV), and human papilloma (HPV) have been shown to be important in the development of hepatocellular carcinoma, lymphoma, and cervical cancer, respectively. However, due to the immunosuppression of patients diagnosed with cancer, the immune systems of these patients often fail to respond to the tumor antigens.

In some embodiments of the methods described herein, the methods further comprise admininstering a chemotherapeutic agent to the subject being administered the bispecific or multispecific polypeptide agent that is specific for PD-1 and TIM-3. Non-limiting examples of chemotherapeutic agents can include include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE®

Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above. In addition, the methods of treatment can further include the use of radiation.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the bispecific or multispecific polypeptide agents described herein to a subject in order to alleviate a symptom of persistent infection. As used herein, "alleviating a symptom of a persistent infection" is ameliorating any condition or symptom associated with the persistent infection. Alternatively, alleviating a symptom of a persistent infection can involve reducing the infectious microbial (such as viral, bacterial, fungal or parasitic) load in the subject relative to such load in an untreated control. As compared with an equivalent untreated control, such reduction or degree of prevention is at least 5%, 10%, 20%, 40%, 50%, 60%, 80%, 90%, 95%, or 100% as measured by any standard technique. Desirably, the persistent infection is completely cleared as detected by any standard method known in the art, in which case the persistent infection is considered to have been treated. A patient who is being treated for a persistent infection is one who a medical practitioner has diagnosed as having such a condition. Diagnosis can be by any suitable means. Diagnosis and monitoring can involve, for example, detecting the level of microbial load in a biological sample (for example, a tissue biopsy, blood test, or urine test), detecting the level of a surrogate marker of the microbial infection in a biological sample, detecting symptoms associated with persistent infections, or detecting immune cells involved in the immune response typical of persistent infections (for example, detection of antigen specific T cells that are anergic and/or functionally impaired).

The term "effective amount" as used herein refers to the amount of a bispecific or multispecific polypeptide agent having specificity for PD-1 and TIM-3, needed to alleviate at least one or more symptom of the disease or disorder, and relates to a sufficient amount of pharmacological composition to provide the desired effect, i.e., reverse the functional exhaustion of antigen-specific T cells in a subject having a chronic immune condition, such as cancer or hepatitis C. The term "therapeutically effective amount" therefore refers to an amount of a a bispecific or multispecific polypeptide agent using the methods as disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the bispecific or multispecific polypeptide agent), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9);

and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

EXAMPLES

The immune response plays an important role in staving off cancer; however, mechanisms of immunosuppression hinder productive anti-tumor immunity. T cell dysfunction or exhaustion in tumor bearing hosts is one such mechanism. PD-1 has been identified as a marker of exhausted T cells in chronic disease states and blockade of PD-1/PD-1L interactions has been shown to partially restore T cell function. The inventors have discovered that Tim-3 is expressed on CD8+ tumor-infiltrating lymphocytes (TILs) in mice bearing solid tumors. All Tim-3+ TILs co-express PD-1 and Tim-3+PD-1+ TILs represent the predominant fraction of T cells infiltrating tumors. Tim-3+PD-1+ TILs exhibit the most severe exhausted phenotype as defined by failure to proliferate, or by failure to produce IL-2, TNFα and IFNγ. The inventors further find that combined targeting of the Tim-3 and PD-1 pathways is more effective in controlling tumor growth than targeting either pathway alone.

The importance of the immune system in protection against cancer was originally proposed in the theory of "cancer immunosurveillance". This theory holds that the immune system can recognize cancerous cells as they arise and can mount both innate and adaptive immune responses to eliminate them. In support of "cancer immunosurveillance" is the fact that both immunodeficient or immunosuppressed patients and experimental animals are more susceptible to tumor development (reviewed in (Dunn et al. 2004; Zitvogel et al. 2006; Swann and Smyth 2007)). Counter to the role of the immune system in staving off cancer, is the ability of tumors to escape the immune system by engendering a state of immunosuppression (Zitvogel et al. 2006). One example of a mechanism of immunosuppression present in tumor-bearing hosts is the promotion of T cell dysfunction or exhaustion.

T cell exhaustion describes a state of T cell dysfunction that was initially observed during chronic lymphocytic choriomeningitis virus (LCMV) infection in mice (Zajac et al. 1998). Exhausted T cells fail to proliferate and exert effector functions such as cytotoxicity and cytokine secretion in response to antigen stimulation. Further studies identified that exhausted T cells are characterized by sustained expression of the inhibitory molecule programmed cell death 1 (PD-1) and that blockade of PD-1 and PD-1 ligand (PD-L1) interactions can reverse T cell exhaustion and restore antigen specific T cell responses in LCMV infected mice (Barber et al. 2006). T cell exhaustion also occurs during chronic infections in humans (reviewed (Klenerman and Hill 2005)) and CD8+ T cells in humans chronically infected with HIV (Day et al. 2006; Petrovas et al. 2006) (Trautmann et al. 2006), hepatitis B virus (HBV) (Boettler et al. 2006) and hepatitis C virus (HCV) (Urbani et al. 2006) express high levels of PD-1. Blocking of PD-1/PD-L interactions in these cells can restore T cell function in vitro.

Several lines of evidence also implicate the PD-1/PD-L pathway in T cell exhaustion in cancer. First, PD-1 expression is found on tumor infiltrating CD8+ T cells in multiple solid tumors (Blank et al. 2006; Ahmadzadeh et al. 2009; Gehring et al. 2009) and on antigen specific CD8+ T cells in hosts with non-solid tumors (Yamamoto et al. 2008; Mumprecht et al. 2009). Second, these PD-1+ T cells are dysfunctional. Third, PD-L1 is expressed at high levels in several different cancers (Latchman et al. 2001; Dong et al. 2002; Brown et al. 2003) and high expression of PD-L1 on tumors is strongly associated with poor prognosis (Thompson et al. 2006). Lastly, interference with PD-1/PD-L signaling either through antibody blockade or PD-1 deficiency has been shown to improve clinical outcome and restore functional T cell responses in several cancers (Blank et al. 2006; Yamamoto et al. 2008; Mumprecht et al. 2009; Zhang et al. 2009).

However, targeting the PD-1/PD-L1 pathway does not always result in reversal of T cell exhaustion (Blackburn et al. 2008; Gehring et al. 2009) and PD-1 expression is not always associated with exhausted phenotype (Petrovas et al. 2006; Fourcade et al. 2009), indicating that other molecules are likely involved in T cell exhaustion.

A recent study in patients with HIV has shown that the immune regulator T cell immunoglobulin-3 (TIM-3) is upregulated on exhausted CD8+ T cells (Jones et al. 2008). Tim-3 is a molecule originally identified as being selectively expressed on IFN-γ secreting Th1 and Tc1 cells (Monney et al. 2002). Interaction of Tim-3 with its ligand, galectin-9, triggers cell death in Tim-3+ T cells. Thus, both Tim-3 and PD-1 can function as negative regulators of T cell responses. In HIV patients, TIM-3 and PD-1 mark distinct populations of exhausted cells with cells positive for both PD-1 and TIM-3 comprising the smallest fraction (Jones et al. 2008) of CD8+ T cells. Similarly, another group has shown that TIM-3 is upregulated on exhausted T cells in patients with HCV (Golden-Mason et al. 2009). In this case, cells that co-express TIM-3 and PD-1 are the most abundant fraction among HCV-specific CD8+ T cells. In both studies, blocking TIM-3 restored T cell proliferation and enhanced cytokine production.

Since targeting the PD-1/PD-L pathway alone does not result in complete restoration of T cell function (Blackburn et al. 2008) and in some cancers targeting the PD-1/PD-L pathway does not restore T cell function at all (Gehring et al. 2009), there is a need to identify other molecules and inhibitory pathways that are involved in T cell exhaustion. Indeed, one study has identified LAG-3 as being expressed on exhausted T cells and although treatment with anti-LAG-3 alone did not restore T cell function in LCMV infected mice, it synergized with PD-1 blockade to improve T cell responses and reduce viral load (Blackburn et al. 2009). Unfortunately, this study did not identify whether LAG-3 and PD-1 are expressed on distinct or overlapping populations of exhausted T cells.

The inventors report herein the co-expression of Tim-3 and PD-1 on a large fraction of tumor infiltrating lymphocytes (TILs) in mice bearing solid tumors. TILs that co-express Tim-3 and PD-1 predominate among CD8+ TILs and exhibit the most profound defects in T cell effector function. The inventors further show that combined targeting of the Tim-3 and PD-1 pathways is highly effective in controlling tumor growth.

Tim-3 and PD-1 Co-Expression on T Cells in Cancer

Figure 1B:
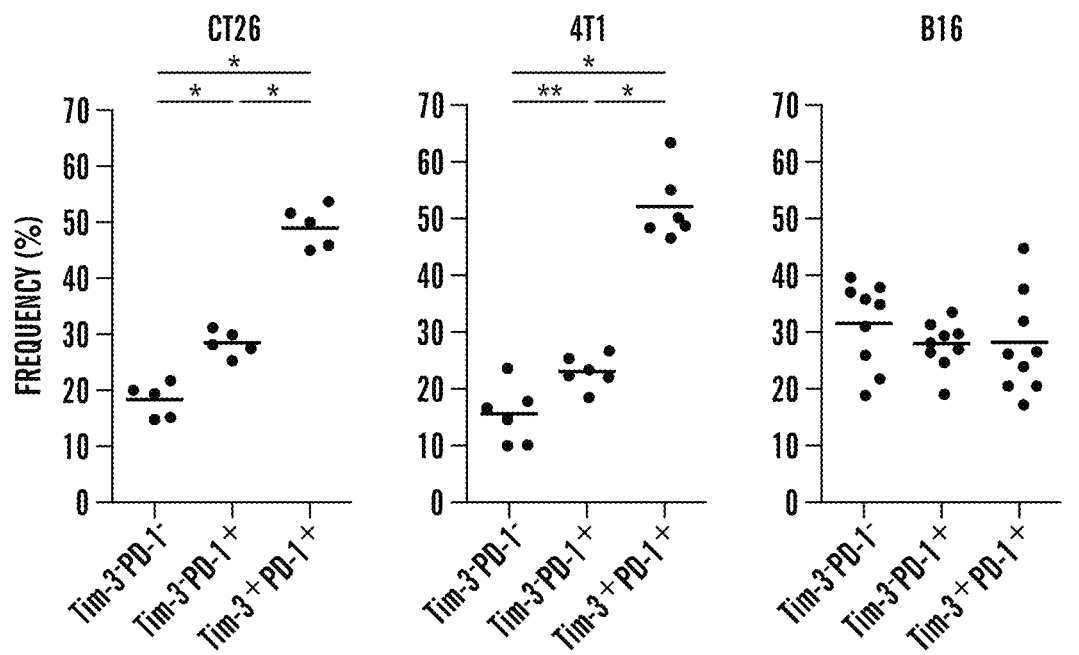

To examine a potential role for Tim-3 in T cell exhaustion in cancer, the expression of Tim-3 as well as PD-1 in T cells from mice bearing the solid tumor CT26 colon was first examined. Among CD8+ carcinoma tumor infiltrating lymphocytes (TILs), it was observed that cells that co-express Tim-3 and PD-1 comprise the major population (~50%) with cells expressing PD-1 alone or neither Tim-3 or PD-1 comprising smaller populations (~30% and ~20%, respectively) (FIGS. 1A and 1B). To extend these observations to other cancers, the CD8+ TILs in mice bearing other solid tumors were examined: 4T1 mammary adenocarcinoma and B16F10 melanoma. In line with the observations in mice bearing CT26, cells that co-express Tim-3 and PD-1 also comprise ~50% of the CD8 TILs in mice bearing 4T1 tumor with cells expressing PD-1 alone or neither Tim-3 or PD-1 also comprising smaller populations (~25% and ~15%, respectively) (FIG. 1B). In mice bearing B16F10 melanoma, all three populations of CD8+ TILs (Tim-3⁻PD-1⁻, Tim-3⁺PD-1⁺ and Tim-3⁻PD-1⁺) are roughly present at equal frequency. Interestingly, in all three of the tumor models examined any Tim-3⁺PD-1⁻ TILs were not observed (FIG. 1A). CD4+ TILs were also examined; however, these are less abundant and among these it was found that the majority were Tim-3⁻PD-1⁻ with the Tim3+PD-1+ and Tim-3⁻PD-1⁺ populations being roughly equivalent (FIG. 1A). Collectively, these data indicate that Tim-3 and PD-1 co-expressing CD8+ TILs comprise a major population of T cell present in TILs infiltrating different solid tumors.

Figure 1C:
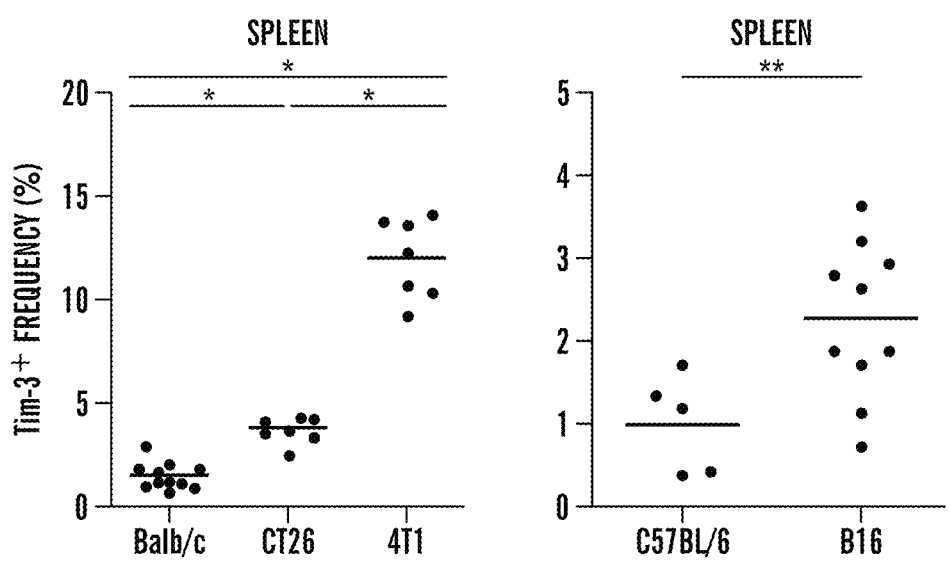
Figure 6:
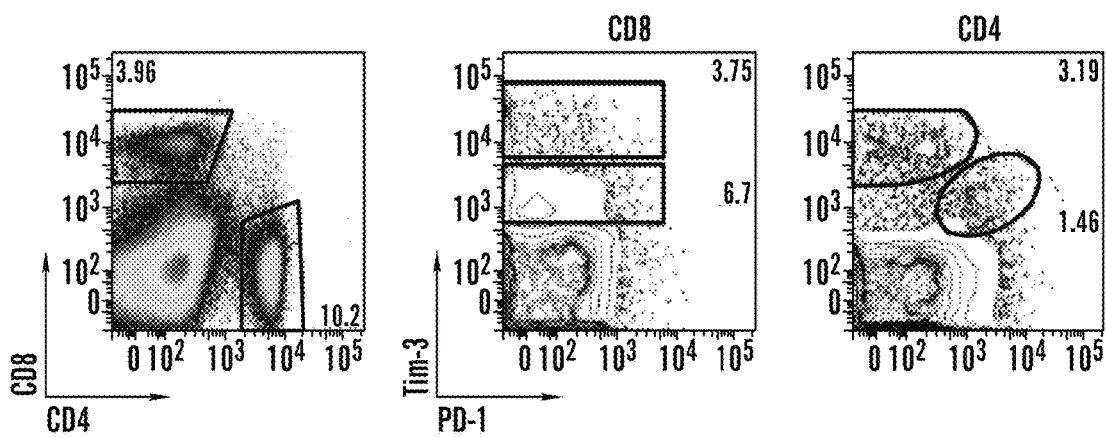
FIG. 6 demonstrates Tim-3 and PD-1 expression in spleen of tumor-bearing mice. Balb/c mice were implanted with CT26 colon adenocarcinoma. Spleen cells were harvested and stained with 7AAD to exclude dead cells and antibodies against CD8, CD4, Tim-3 and PD-1. Expression of Tim-3 and PD-1 on gated CD4+ and CD8+ cells is shown. Data shown are representative of 5 independent analyses.

Tim-3 and PD-1 expression was also examined in the spleens of tumor-bearing mice. Here a trend towards increased frequency of CD8+Tim-3+ cells compared to naïve mice was observed; however, the extent of this increase was variable among mice bearing different solid tumors (FIG. 1C). In contrast to the CD8+ TILs, little, if any, evidence was found for co-expression of PD-1 with Tim-3 among splenic CD8T cells in tumor-bearing mice (FIG. 6), suggesting that upregulation of PD-1 on CD8 Tim-3⁻ cells can happen specifically in the tumor environment in response to environmental cues. However, two distinct populations of Tim-3+ cells, Tim-3$^{high}$ and Tim-3$^{low}$ in the peripheral lymphoid tissue of tumor bearing mice were distinguished. Similarly, among splenic CD4+ T cells in tumor bearing mice, a Tim-3$^{high}$ and Tim-3$^{low}$ population was observed. Interestingly, the Tim-3$^{low}$ population was characterized by co-expression of PD-1, suggesting that these cells could be the precursors of Tim-3⁺PD-1⁺ TILs and that they could represent T cells that are in a different functional state from Tim-3$^{high}$ cells (FIG. 6).

T Cell Dysfunction in TILs Expressing Tim-3 and PD-1

Figure 2A:
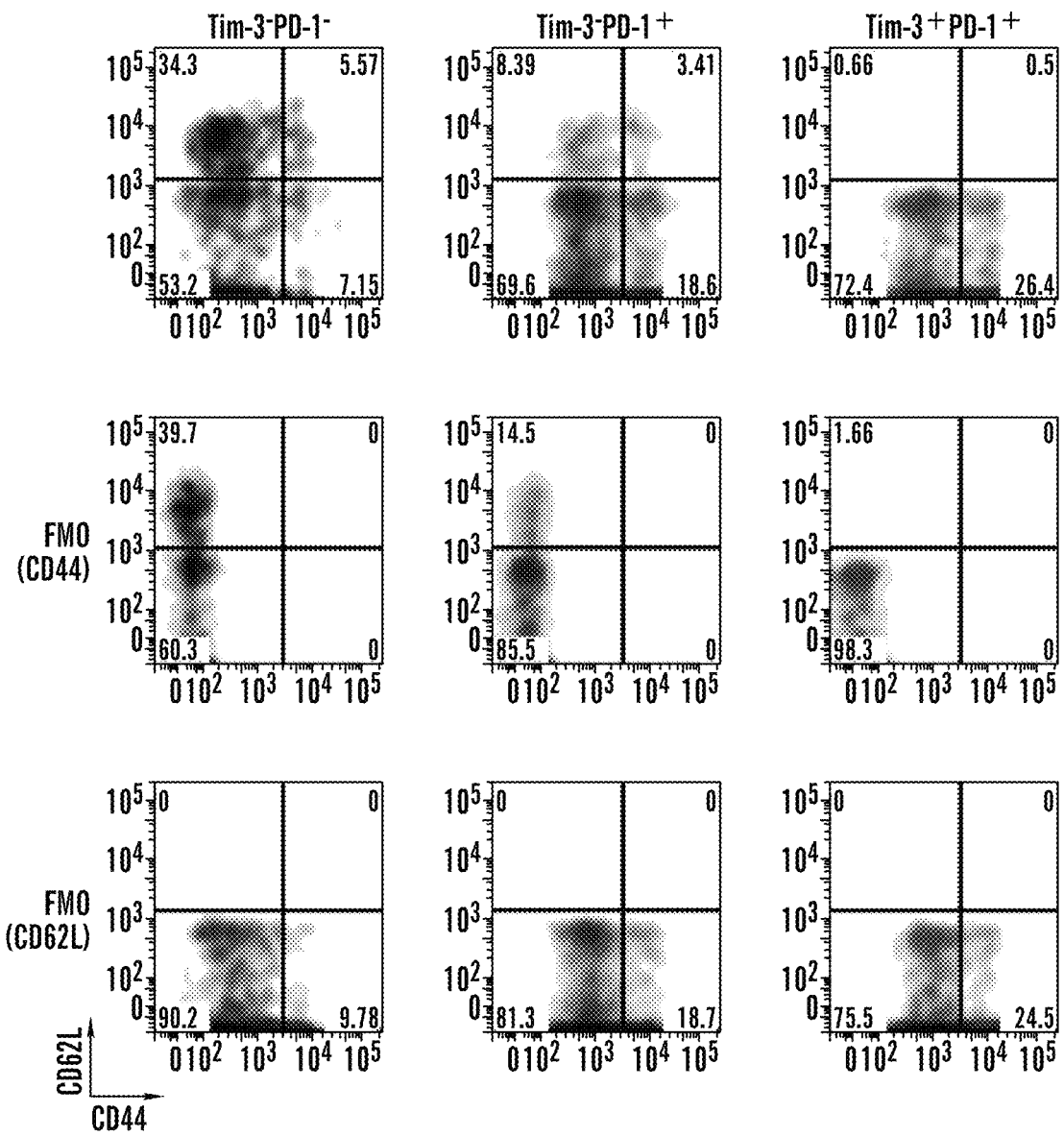
FIGS. 2A and 2B demonstrate CD44 and CD62L expression in Tim-3 and PD-1 expressing TILs. TILs were harvested from CT26 tumor-bearing mice and stained with 7AAD, to exclude dead cells, and antibodies against CD8, CD44, CD62L, Tim-3, and PD-1.
Figure 2B:
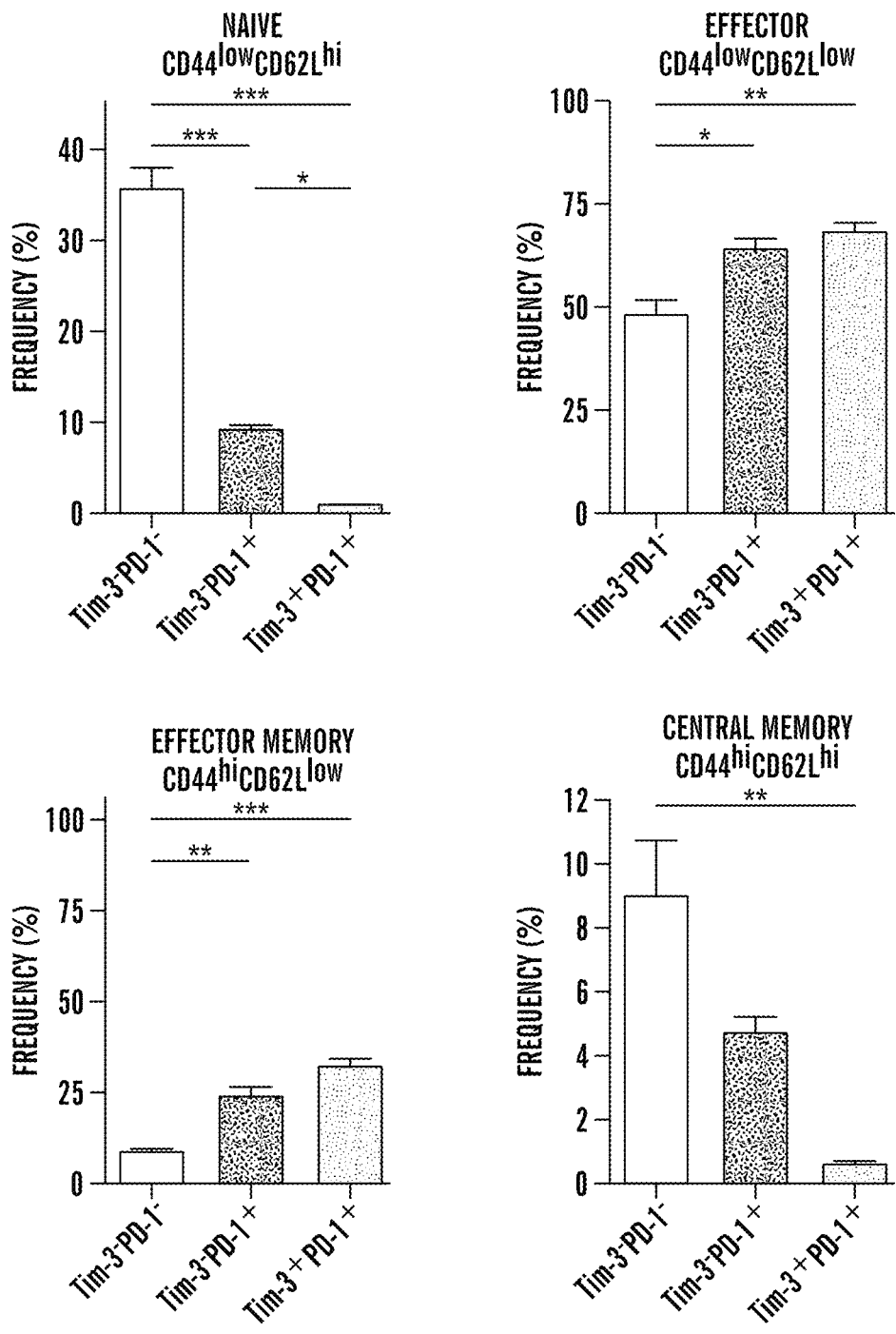

To further characterize the different subsets of CD8+ TILs, their expression of CD44 and CD62L was first examined. It was found that the pattern of CD62L and CD44 expression was quite different among the Tim-3-PD-1-, Tim-3-PD-1+ and Tim-3+PD-1+ TILs. All three populations of TILs expressed high levels of CD44 (FIGS. 2A and 2B). However, only the Tim-3-PD-1− and Tim-3− PD-1+ TILs contained naïve (CD44$^{low}$ CD62L$^{hi}$) T cells, with the Tim-3⁻PD-1⁻ TILs containing the highest proportion of naïve T cells (~35%). Among the Tim-3⁺PD-1⁺ TILs, the majority were CD62L$^{low}$ and the fraction of central memory (CD44$^{hi}$CD62L$^{hi}$) cells was lowest in this population. These data gave the first indication that the three populations of TILs characterized by differential expression of Tim-3 and PD-1 contain cells in different functional states.

Figure 3A:
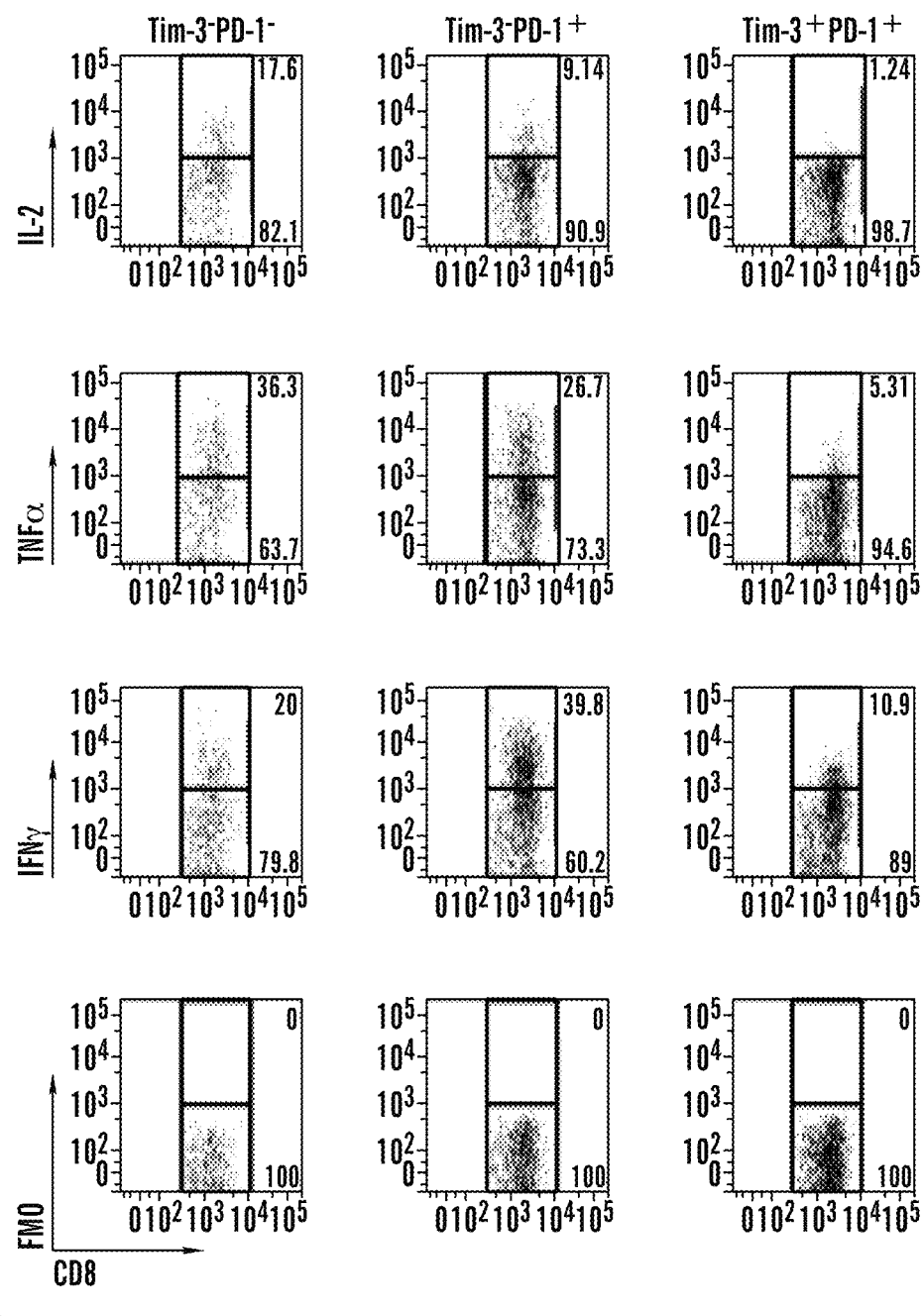
FIGS. 3A-3B demonstrate cytokine production in TILs from CT26 tumor-bearing mice. TILs were harvested from CT26 tumor-bearing mice and stimulated with PMA and Ionomycin prior to intracytoplasmic cytokine staining.

In chronic viral infection, PD-1 has been identified as a marker of dysfunctional or exhausted CD8⁺ T cells (Barber et al. 2006). Furthermore, it has been observed that there is a hierarchy of T cell exhaustion with CTL function and production of IL-2 being compromised first, followed by loss of TNF and then IFN (Wherry et al. 2003). Therefore, to determine whether any of the Tim-3 and PD-1 expressing TILs exhibited exhausted phenotype, CD8+ TILs were isolated and their production of IL-2, TNFα, and IFNγ was examined directly ex vivo. It was found that the Tim-3+PD-1+ TILs exhibited the most profound impairment in production of IL-2, TNFα, and IFNγ when compared to Tim-3−PD-1+ TILs and Tim-3−PD-1− TILs (FIG. 3A).

Figure 3B:
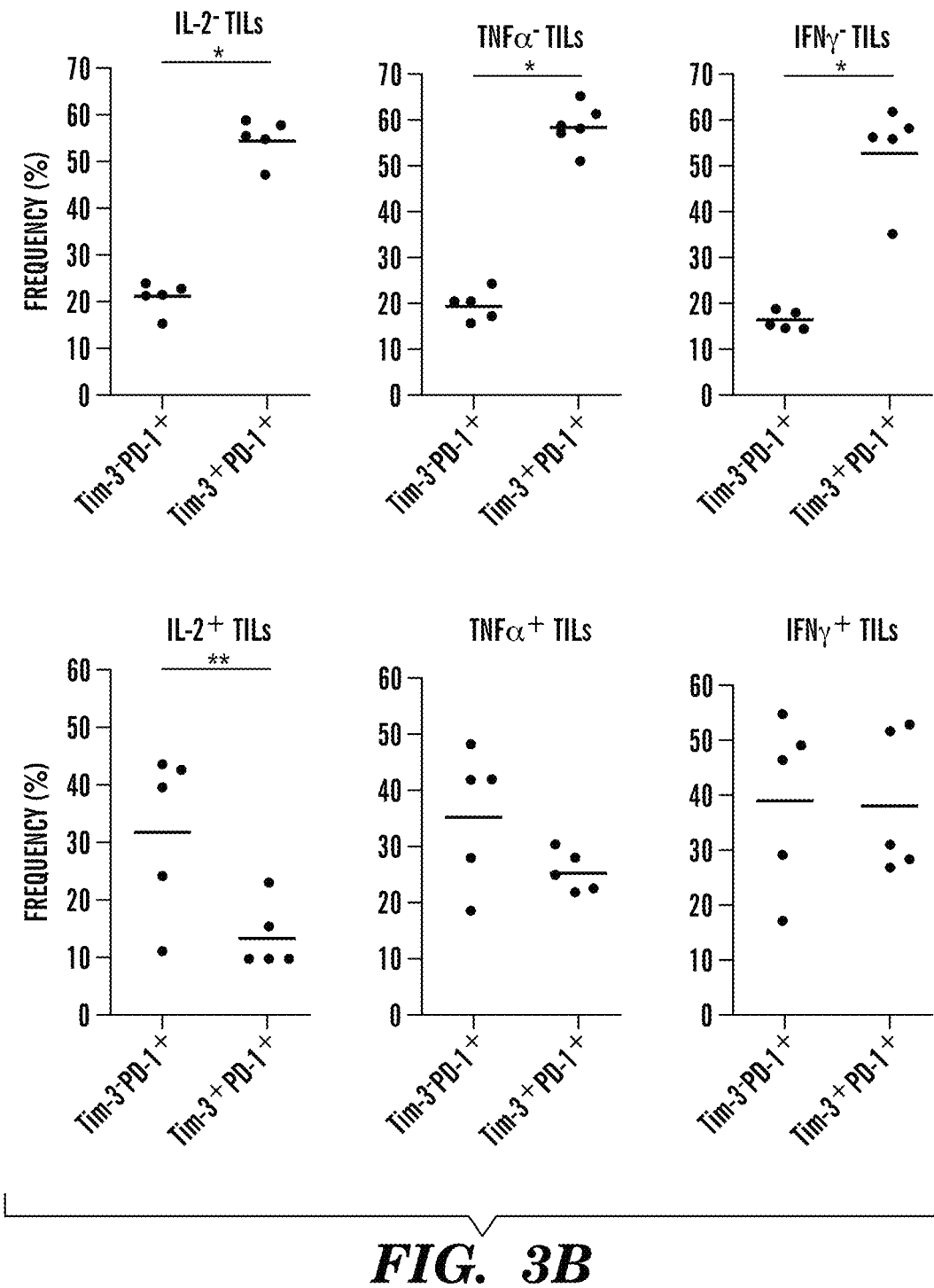

Surprisingly, the Tim-3−PD-1+ TILs produced the most IFNγ among the three populations of TILs and showed significantly less impairment in the production of IL-2 and TNFα than the Tim-3+PD-1+ TILs. These data suggest that the Tim-3+PD-1+ TILs represent the most exhausted TILs and that Tim-3−PD-1+ TILs could contain a mixture of exhausted T cells and effector T cells. To further confirm these observations, the abundance of Tim-3+PD-1+ cells and Tim-3−PD-1+ cells was determined within the cytokine producing and non-producing TILs (FIG. 3B). It was found that Tim-3+PD-1+ cells are the most abundant (55-60%) population among cytokine non-producing TILs, outnumbering Tim-3−PD-1+ cells by 3-4 fold. Examination of cytokine-producing TILs revealed that Tim-3+PD-1+ cells are less abundant than Tim-3−PD-1+ among IL-2-producing TILs. A similar trend was observed with TNFα, although this did not reach statistical significance. Both populations were equally represented among IFNγ producing TILs. Interestingly, this stepwise loss in abundance of Tim-3+PD-1+ cells among cytokine producing TILs seems to follow the hierarchy of T cell exhaustion, suggesting that exhaustion is likely a dynamic process in vivo and that Tim-3+PD-1+ cells could be the first to develop an exhausted phenotype.

Figure 4B:
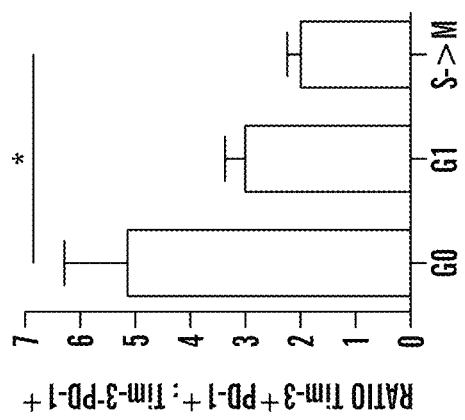
FIGS. 4A-4B demonstrate proliferation and cell cycle entry in TILs from CT26 tumor-bearing mice. TIL s were harvested from CT 26 tumor-bearing mice and stimulated with anti-CD3 (1 g/ml) prior to staining with antibodies against CD8, Tim-3, PD-1 and Ki-67 and TO-PRO-3-iodide.
Figure 4A:
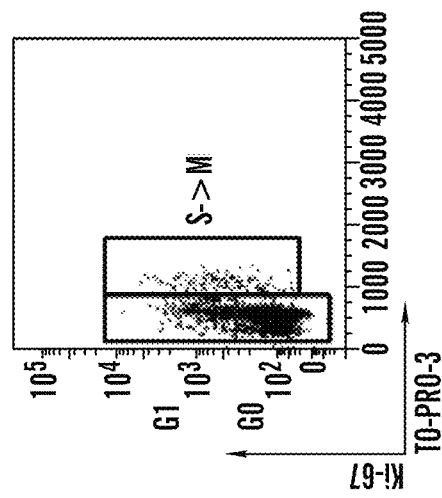

As stated above, loss of the ability to proliferate in response to TCR stimulation is among the first effector functions lost in exhausted T cells. The ability of TILs to proliferate directly ex vivo was therefore examined by determining expression of Ki-67, a nuclear protein expressed by cells that have entered into cell cycle. However, it has been noted that in individuals chronically infected with HIV, cells that are arrested in G1 can express Ki-67+ (Combadere et al. 2000). DNA content was also examined by simultaneously staining with TO-PRO-3 iodide. By doing so, cells arrested in G1 can be discerned from cells that have progressed to S, G2 and M phase. TILs were isolated and stimulated directly ex vivo prior to examination of Ki-67 expression and DNA content. The abundance of Tim-3+PD-1+ and Tim-3−PD-1+ cells in G0, G1 and S-M phases of cell cycle was then determined (FIG. 4A). It was found that Tim-3+PD-1+ cells are the most abundant population that is stuck in G0, outnumbering Tim-3−PD-1+ cells by 5 to 1 (FIG. 4B). Interestingly, when cells that have progressed to the G1 and S-M phases were examined, it was found that Tim-3+PD-1+ cells steadily decrease in number while Tim-3−PD-1+ cells steadily increase with progression through cell cycle. Collectively, the data strongly support that co-expression of Tim-3 and PD-1 marks the most exhausted population of TILs, which fail to proliferate, produce IL-2, TNFα, and IFNγ.

Effect of Targeting the Tim-3 and PD-1 Signaling Pathways in Cancer

Figure 5A:
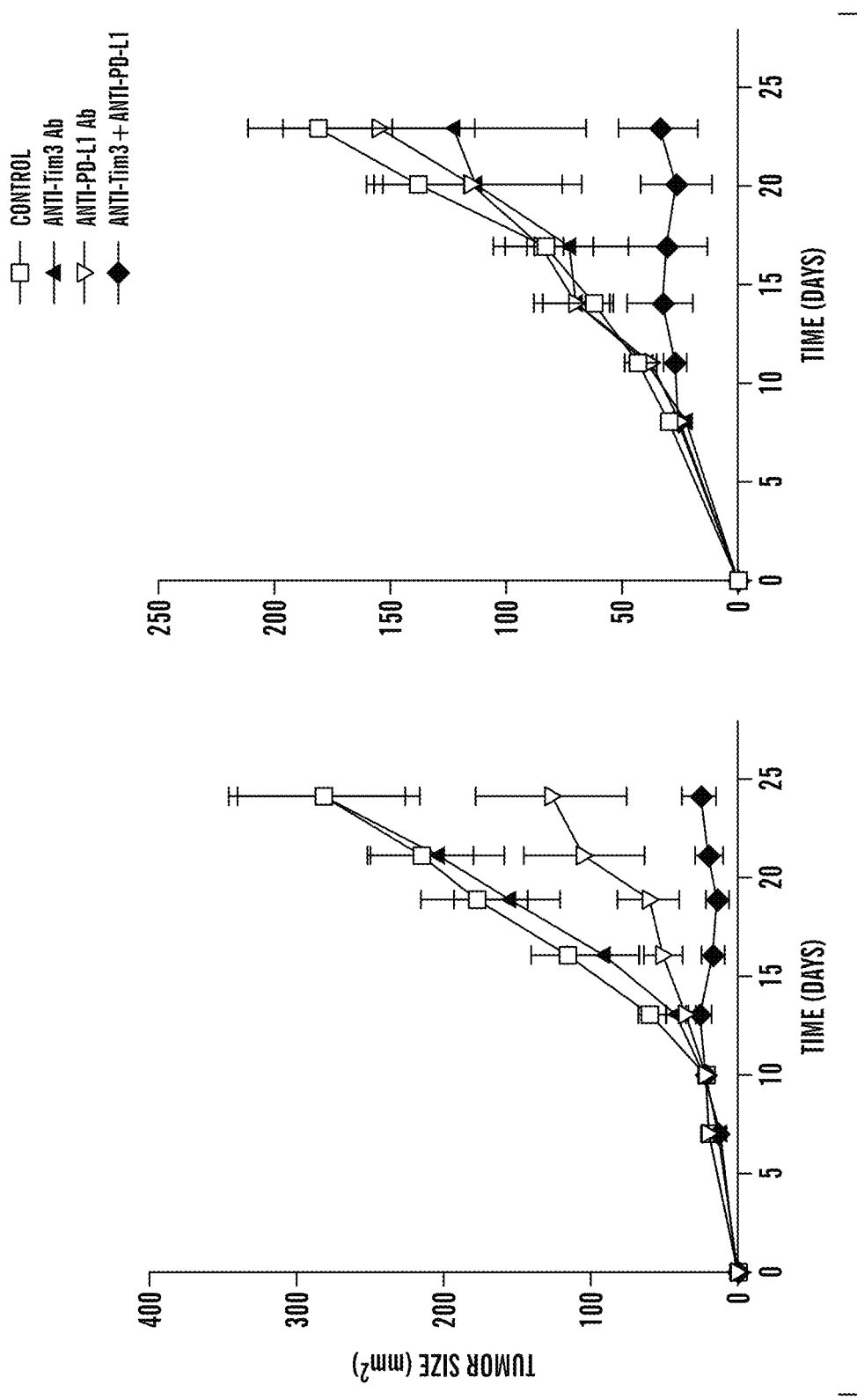
FIGS. 5A-5B demonstrate the effect of co-targeting the Tim-3 and PD-1 signaling pathways on tumor growth.
Figure 5B:
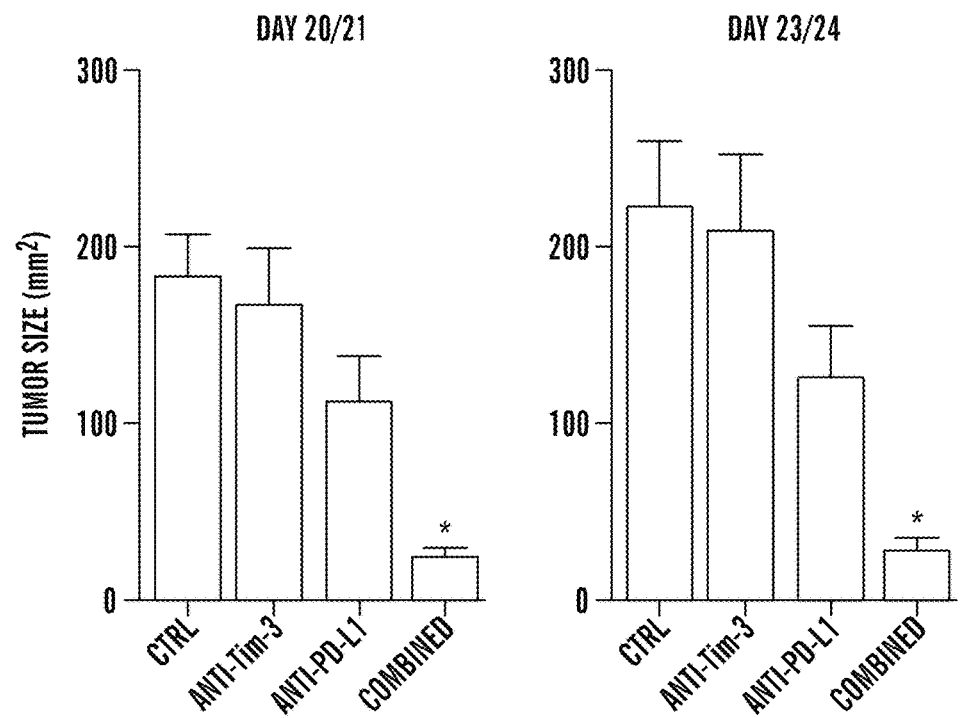
Figure 7:
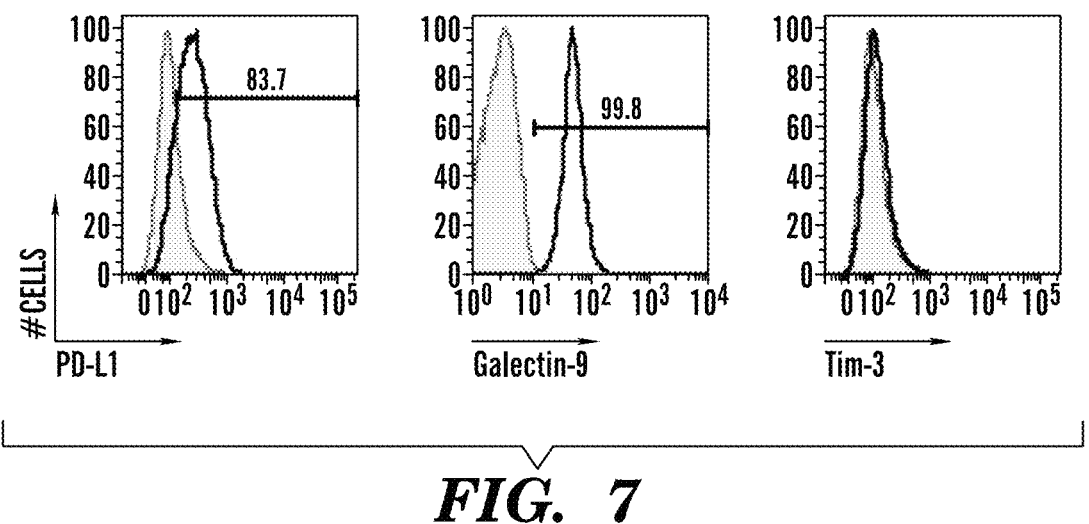
FIG. 7 demonstrates expression of PD-L1, Tim-3 and Galectin-9 on CT26 tumor cells. CT26 tumor cells were stained with antibodies against PD-L1, galectin-9 or Tim-3 (open histogram). Fluorescence minus one (FMO) staining (shaded histogram). Data are representative of two independent experiments.
Figure 8:
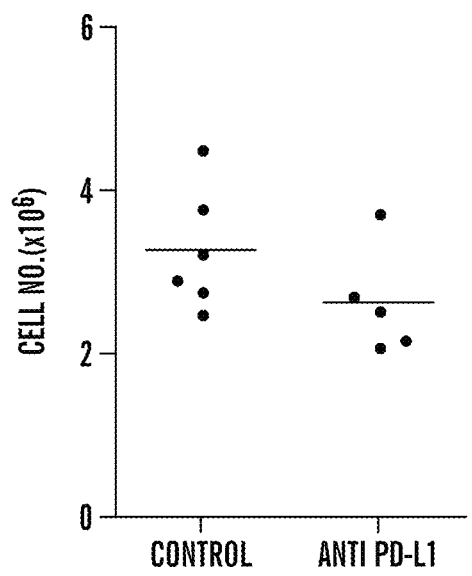
FIG. 8 demonstrates effects of antibodies on tumor growth in vitro. CT26 tumor cells (1×106) were cultured in vitro for 48 hrs in the presence of 10 µg/ml anti-PD-L1 antibody or isotype control. Viable cells were quantified by trypan blue exclusion at the end of the culture period. Each point represents an independent culture well. Data are representative of two independent experiments.

These demonstrations along with the previous observations that blockade of either the PD-1 or Tim-3 (Jones et al. 2008; Golden-Mason et al. 2009) signaling pathways can improve T cell function in the context of chronic infections raised the possibility that combined targeting of these two pathways can prove to be the most efficacious means to restore anti-tumor immunity in vivo. Before commencing in vivo treatments, the expression of the PD-1 and Tim-3 ligands (PD-L1 and galectin-9, respectively) on CT26 tumor (FIG. 7) was first confirmed. CT26 tumor-bearing mice were then treated with an anti-Tim-3 antibody that was previously described to have blocking function in vivo (Monney et al. 2002), anti-PD-L1 antibody, anti-Tim-3 plus anti-PD-L1 antibodies, or control immunoglobulins. It was found that treatment with anti-Tim-3 alone had little or no effect and treatment with anti-PD-L1 alone showed a trend towards delayed tumor growth; however, this varied between experiments and did not reach statistical significance (FIG. 5). However, combined treatment with anti-Tim-3 and anti-PD-L1 resulted in a dramatic reduction in tumor growth with 50% of the mice exhibiting complete tumor regression. Since CT26 tumor expresses PD-L1 but not Tim-3 (FIG. 7), the possibility that anti-PD-L1 antibody could have direct inhibitory effects on tumor growth was controlled for. CT26 tumor was cultured in the presence of anti-PD-L1 or control immunoglobulin and it was found that tumor proliferation was not affected (FIG. 8). The effect of anti-Tim-3 plus anti-PD-L1 treatment in mice bearing B16 melanoma was also tested, and it was found that mice receiving the combined treatment exhibit enhanced survival relative to control immunoglobulin, anti-Tim-3, or anti-PD-L1-treated mice.

Figure 9:
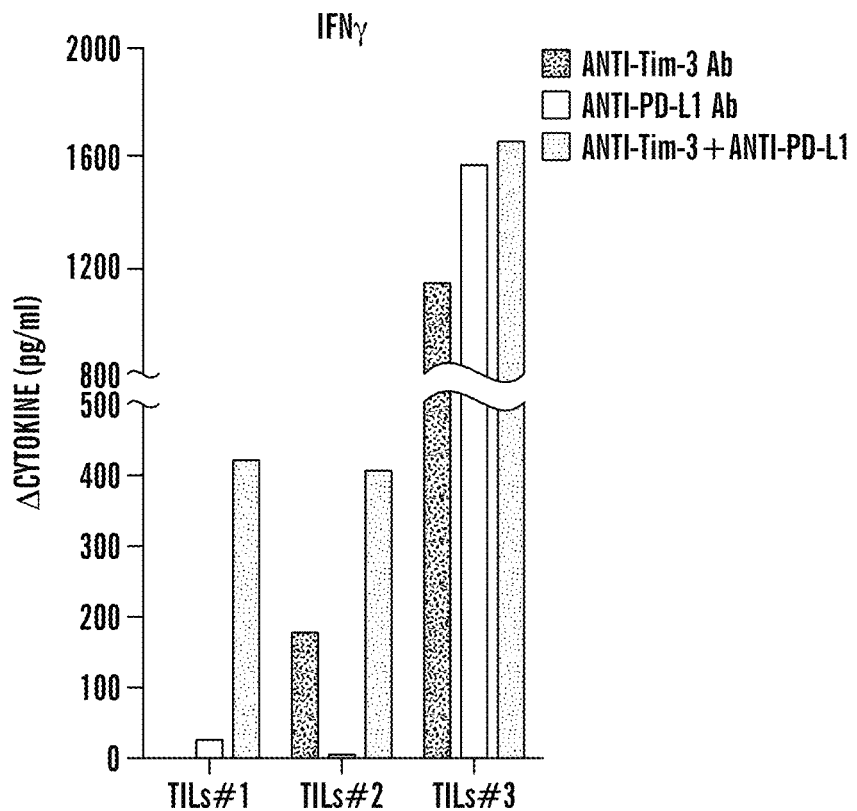
FIG. 9 demonstrates that combined blockade of the Tim-3 and PD-1 signaling pathways restores IFNγ production. TILs were harvested from CT26 tumor-bearing mice and cultured in vitro in the presence of soluble anti-CD3 and either anti-Tim-3, anti-PD-L1, anti-Tim-3 plus anti-PD-L1 or control immunoglobulins. After 96 hours, culture supernatant was collected and IFNγ measured by cytometric bead array (CBA). Data are expressed as the difference in cytokine production over that observed in cultures with control immunoglobulins. Data shown are from three independent TILs samples from two independent experiments.
Figure 10:
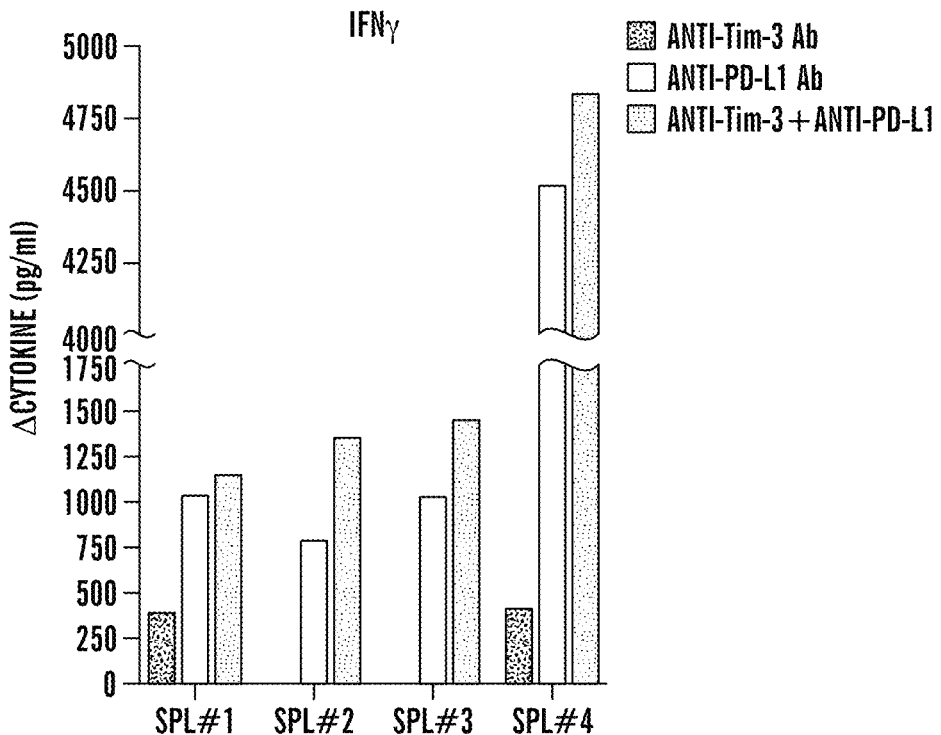
FIG. 10 shows the effect of co-targeting both the Tim-3 and PD-1 signaling pathways on peripheral T cell responses. Splenocytes from CT26 tumor-bearing mice were cultured ($3 \times 10^5$/well) in the presence of anti-CD3 (5 µg/ml) and 10 µg/ml of either anti-Tim-3, anti-PD-L1, anti-Tim-3 plus anti-PD-L1, or control immunoglobulins. After 96 hours, culture supernatant was collected and IFNγ measured by cytometric bead array (CBA) (BD Biosciences). Data are expressed as the difference in cytokine production over that observed in cultures with control immunoglobulins. Data shown are from two independent experiments.

To address directly whether treatment with anti-Tim-3 plus anti-PD-L1 indeed restores TILs function, TILs from mice bearing CT26 tumor were isolated and cultured in the presence of anti-Tim-3, anti-PD-L1, anti-Tim-3 plus anti-PD-L1 antibodies, or control immunoglobulins (FIG. 9). It was found that while both anti-Tim-3 and anti-PD-L1 alone were able to augment IFNγ production from TILs, this effect was variable and often weaker when compared to the increase in IFNγ production observed in TILs treated with both anti-Tim-3 and anti-PD-L1 antibodies. Indeed, these data parallel closely what was observed in in vivo treatment experiments, where anti-Tim-3 or anti-PD-L1 alone have a limited and/or variable effect on tumor growth (FIG. 5). The effect of anti-Tim-3 plus anti-PD-L1 treatment on peripheral T cell responses from tumor-bearing mice was also examined and it was found that, similar to the effects observed on TILs, both anti-Tim-3 and anti-PD-L1 alone had a variable and often weaker effect on IFNγ production relative to the effect of anti-Tim-3 plus anti-PD-L1 (FIG. 10).

Figure 11:
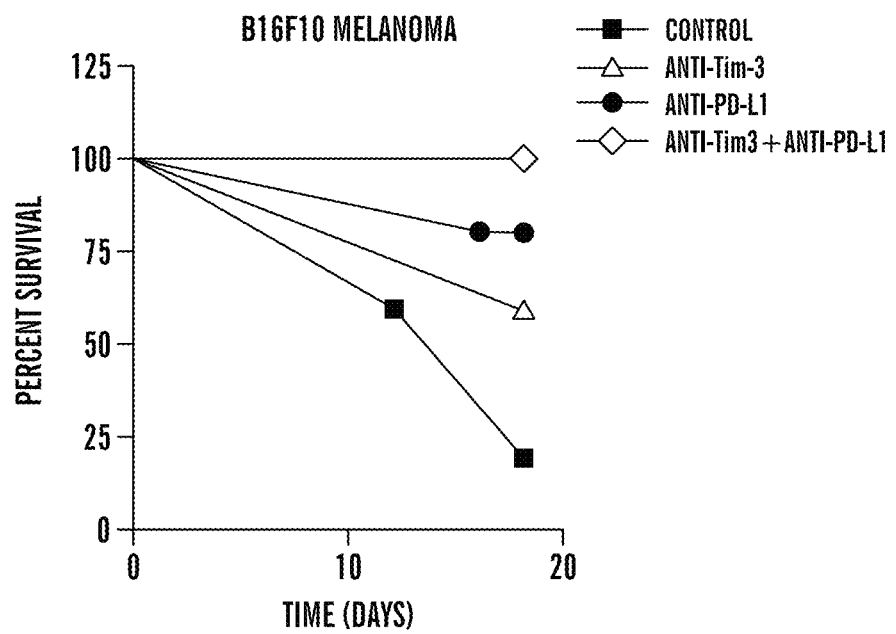
FIG. 11 demonstrates that combined targeting of Tim-3 and PD-1 pathways increases survival in a B16 melanoma model. Female C57BL/6 mice were implanted with B16F10 and treated with either control immunoglobulin, anti-Tim-3 antibody (clone 5D12), anti-PD-L1 antibody (clone 10F.9G2), or both antibodies. Mice were monitored for tumor growth and survival. n=5 per group.

In addition, FIG. 11 demonstrates that combined targeting of Tim-3 and PD-1 pathways dramatically increases survival in a B16 melanoma model. Female C57BL/6 mice were implanted with B16F10 and treated with either control immunoglobulin, anti-Tim-3 antibody (clone 5D12), anti-PD-L1 antibody (clone 10F.9G2), or both antibodies. Mice were monitored for tumor growth and survival. n=5 per group.

Figure 12:
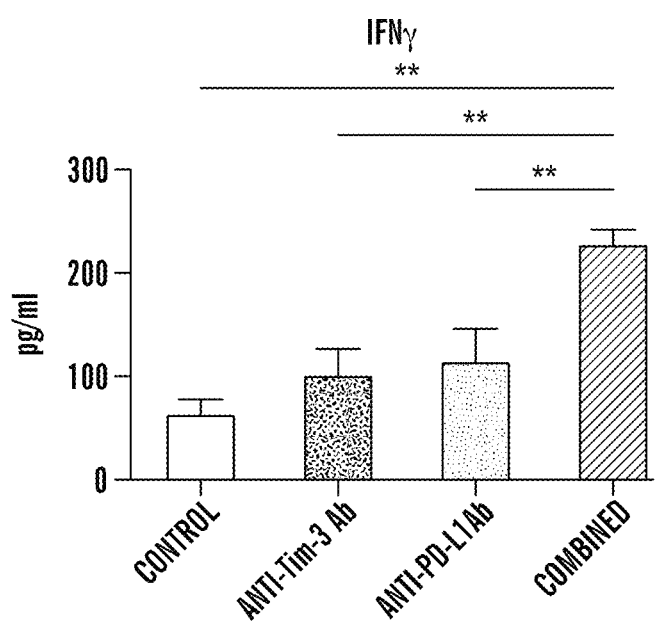
FIG. 12 demonstrates restoration of tumor specific T cell response in mice treated with anti-Tim-3 and anti-PD-L1. Cells from the draining lymph node of Balb/c mice implanted with CT-26 colon carcinoma were treated with either control immunoglobulin, anti-Tim-3 antibody (clone 2C12), anti-PD-L1 antibody (clone 10F.9G2), or both antibodies. Cells from the tumor draining lymph node of treated mice were cultured with the tumor antigen AH1 (30 µg/ml). Production of IFN-γ in supernatant collected at 48 hrs is shown. *p>0.01, **p>0.05, One-way ANOVA, Tukey's multiple comparison test. Data shown are the mean of two independent samples. Similar results were obtained in two additional independent experiments.

Further, FIG. 12 demonstrates restoration of tumor specific T cell response in mice treated with anti-Tim-3 and anti-PD-L1. Cells from the draining lymph node of Balb/c mice implanted with CT-26 colon carcinoma were treated with either control immunoglobulin, anti-Tim-3 antibody (clone 2C12), anti-PD-L1 antibody (clone 10F.9G2), or both antibodies. Cells from the tumor draining lymph node of treated mice were cultured with the tumor antigen AH1 (30 μg/ml). Production of IFN-γ in supernatant collected at 48 hrs is shown. *p>0.01, **p>0.05, One-way ANOVA, Tukey's multiple comparison test. Data shown are the mean of two independent samples. Similar results were obtained in two additional independent experiments. Again, combined treatment dramatically increases the IFN-γ I secretion relative to secretion with either agent alone.

Figure 13:
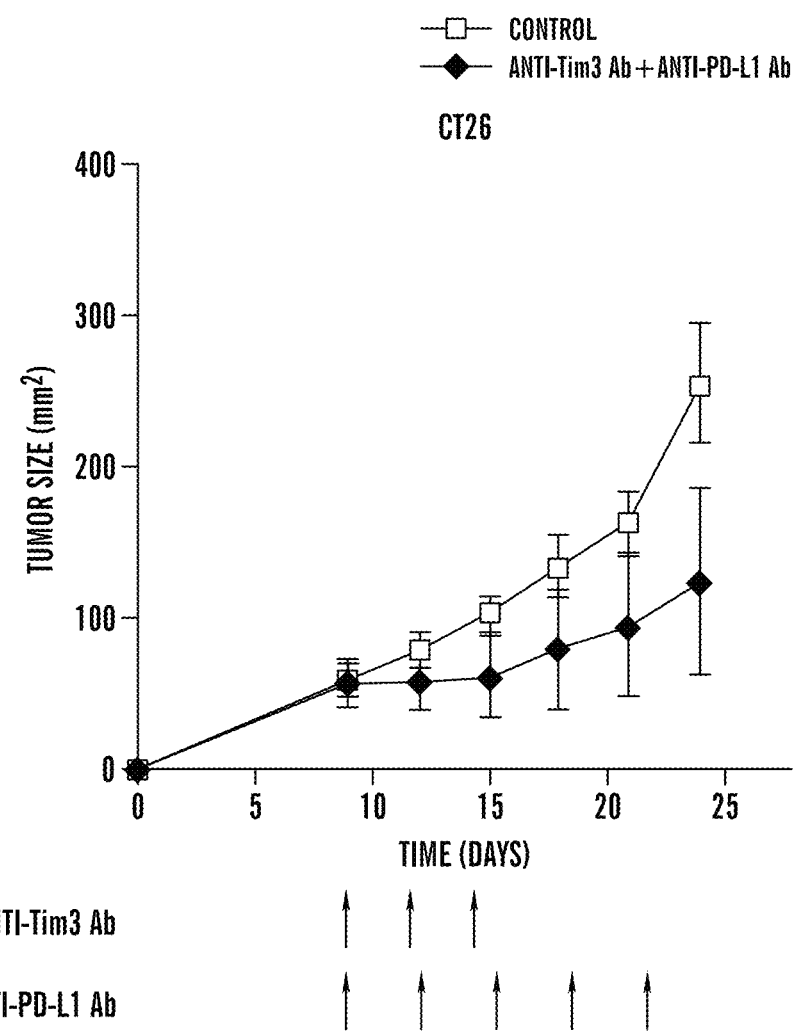
FIG. 13 demonstrates effects of targeting the Tim-3 and PD-1 pathways on established tumors. BALB/c mice were implanted with CT-26 colon carcinoma. Once tumors reached 30-50 mm², mice were treated with either control immunoglobulin or anti-Tim-3 (clone 2C12) plus ant-PD-L1 antibody (clone 10F.9G2). n=5 per group. 2 out of 5 animals in the anti-Tim-3 plus anti-PD-L1 group exhibited complete tumor regression.

Providing further evidence, FIG. 13 demonstrates effects of targeting the Tim-3 and PD-1 pathways on established tumors. BALB/c mice were implanted with CT-26 colon carcinoma. Once tumors reached 30-50 mm2, mice were treated with either control immunoglobulin or anti-Tim-3 (clone 2C12) plus anti-PD-L1 antibody (clone 10F.9G2). n=5 per group. The combination was effective in reducing tumor size relative to untreated control, and significantly, in 2 out of 5 animals in the anti-Tim-3 plus anti-PD-L1 group exhibited complete tumor regression in an established tumor model.

Collectively, the data described herein demonstrates that combined targeting of the Tim-3 and PD-1 signaling pathways is highly effective in restoring anti-tumor immunity.

Aside from the chronicity of disease, little is known about the factors involved in inducing and/or maintaining exhaustion in T cells. PD-1 has been the primary marker for exhausted T cells. However, the data described herein show that PD-1 single positive TILs likely include bonafide effector T cells that produce IFNγ, as this population contains the highest frequency of IFNγ producing cells, even higher than the PD TILs (FIG. 3A). These data indicate that PD-1 is an imperfect marker of exhaustion and that co-expression of Tim-3 clearly marks the T cells with the most exhausted phenotype. However, several questions remain. It is known that triggering of Tim-3 can transmit a death signal into T cells. How then do Tim-3+PD-1+ exhausted T cells persist in chronic conditions? Without wishing to be bound or limited by a theory, one possibility is that differential levels of Tim-3 expression drive different functional outcomes, i.e., high levels of Tim-3 promote T cell death whereas low levels of Tim-3 transmit an inhibitory signal that allows for cells to escape death and persist in a dysfunctional state. In this regard, the presence of Tim-3$^{low}$ cells in both the CD4 and CD8 compartments in the periphery of tumor-bearing mice was observed (FIG. 6). It will be intriguing to determine if these T cells are in a different state of effector function compared to Tim-3$^{high}$ cells. Without wishing to be bound or limited by a theory, a second, non-mutually exclusive possibility is that co expression of PD-1 and/or other inhibitory molecules, such as LAG-3, is responsible or preserving cells with exhausted phenotype. Without wishing to be bound or limited by a theory, a third non-mutually exclusive possibility is that the decision between exhaustion and death could be regulated at the level of availability of Tim-3 ligand, galectin-9. In this regard, it still remains to be demonstrated whether development of exhaustion in TILs is dependent on galectin-9 expression on the tumor itself or whether it starts in the periphery and the exhausted phenotype is further amplified by an interaction of Tim-3:Galectin-9 in the tumor.

Aside from the recent implication of the transcription factor Blimp-1 in promoting exhausted phenotype in CD8+ T cells during chronic LCMV infection (Shin et al. 2009), very little is known about the downstream signals that are responsible for inducing and/or maintaining the exhausted phenotype. The novel discovery described herein, where Tim-3+PD-1+ cells were identified as the truly exhausted T cells in chronic conditions facilitates the examination of the gene programs that drive/maintain exhausted phenotype, and provides therapeutic approchaes for stimulating immune activity in chronic immune conditions, such as cancer and infectious diseases.

Materials and Methods

Isolation of Tumor Infiltrating Lymphocytes. Tumor infiltrating lymphocytes were isolated by dissociating tumor tissue in the presence of collagenase D (25 mg/ml) for 20 min prior to centrifugation on a discontinuous Percoll gradient (GE Healthcare). Isolated cells were then used in various assays of T cell function.

Flow Cytometry. Single cell suspensions were stained with antibodies against CD4 (RM4-5), CD8 (53-6.7), PD-1 (RMP1-30), CD44 (IM7), CD62L (MEL-14) (Biolegend), and Tim-3 (8B.2C12) (Ebioscience). 7AAD was used to exclude dead cells. For intracytoplasmic cytokine staining, cells were stimulated in vitro with PMA (50 ng/ml) and ionomycin (1 μg/ml) for 3 hrs in the presence of Golgi plug (BD Biosciences). Cells were then harvested and stained with CD8, Tim-3 and PD-1 prior to fixation and permeabilization. Permeabilized cells were then stained for IL-2 (JES6-5H4), TNFα (MP6-XT22) and IFNγ (XMG1 .2). All data were collected on a BD LsrII (BD Biosciences) and analyzed with FlowJo software (Tree Star).

Ki67 and TO-PRO-3 staining. TILs were harvested and cultured in vitro in the presence of anti-CD3 (1 μg/ml) for 48 hrs. Cells were then stained with antibodies against CD8, PD-1, Tim-3 (8B.2C12) prior to permeabilization and staining with antibody against Ki-67 (Biolegend) and with TO-PRO-3 iodide (Invitrogen). All data were collected on a BD LsrII (BD Biosciences) and analyzed with FlowJo software (Tree Star).

Tumor Experiments. $5\times10^5$ CT26 were implanted into the right flank of wild type Balb/c mice. Mice were treated with either 100 μg of anti-Tim-3 (clone 8B.2C12) ip on days 0, 2 and 4 or 200 μg of anti-PD-L1 (clone 10F.9G2) on days 0, 3, 6, 9 and 12, or isotype control immunoglobulin's (Rat IgG1 and RatIgG2b). Tumor surface was measured in two dimensions using a caliper.

In vitro Experiments. Tumor infiltrating lymphocytes were harvested as described and cultured ($1-3\times10^5$/well) in the presence of soluble anti-CD3 (5 μg/ml) and 10 μg/ml of either anti-Tim-3 (clone 8B.2C12), anti-PD-L1 (clone 10F.9G2), both anti-Tim-3 plus anti-PD-L1 or control immunoglobulins (Rat IgG1 and RatIgG2b). After 96 hours, culture supernatant was collected and IFNγ measured by cytometric bead array (CBA) (BD Biosciences).

REFERENCES

Ahmadzadeh, M., L. A. Johnson, B. Heemskerk, J. R. Wunderlich, M. E. Dudley, D. E. White and S. A. Rosenberg. 2009. Tumor antigen-specific CD8 T cells infiltrating the tumor express high levels of PD-1 and are functionally impaired. Blood. 1 14: 1 537-44.

Barber, D. L., E. J. Wherry, D. Masopust, B. Zhu, J. P. Allison, A. H. Sharpe, G. J. Freeman and R. Ahmed. 2006. Restoring function in exhausted CD8 T cells during chronic viral infection. Nature. 439: 682-7.

Blackburn, S. D., H. Shin, G. J. Freeman and E. J. Wherry. 2008. Selective expansion of a subset of exhausted CD8 T cells by alphaPD-L1 blockade. Proc Natl Acad Sci USA. 105: 15016-21.

Blackburn, S. D., H. Shin, W. N. Haining, T. Zou, C. J. Workman, A. Polley, M. R. Betts, G. J. Freeman, D. A. Vignali and E. J. Wherry. 2009. Coregulation of CD8+ T cell exhaustion by multiple inhibitory receptors during chronic viral infection. Nat Immunol. 10: 29-37.

Blank, C., J. Kuball, S. Voelkl, H. Wiendl, B. Becker, B. Walter, O. Majdic, T. F. Gajewski, M. Thoebald, R. Andreesen and A. Mackensen. 2006. Blockade of PD-L1 (B7-H1) augments human tumor-specific T cell responses in vitro. Int. J. Cancer. 119: 317-27.

Boettler, T., E. Panther, B. Bengsch, N. Nazarova, H. C. Spangenberg, H. E. Blum and R. Thimme. 2006. Expression of the interleukin −7 receptor alpha chain (CD 127) on virus-specific CD8+ T cells identifies functionally and phenotypically defined memory T cells during acute resolving hepatitis B virus infection. J. Virol. 80: 3532-40.

Brown, J. A., D. M. Doifman, F. R. Ma, E. L. Sullivan, O. Munoz, C. R. Wood, E. A. Greenfield and G. J. Freeman . 2003. Blockade of programmed death-1 ligands on dendritic cells enhances T cell activation and cytokine production. J Immunol. 170: 1257-66.

Combadere, B., C. Blanc, T. Li, G. Carcelain, C. Delaugerre, V. Calvez, R. Tubiana, P. Debre, C. Katlama and B. Autran. 2000. CD4+Ki67+ lymphocytes in HIV-infected patients are effector T cells accumulated in the G 1 phase of the cell cycle.EurIImmunol. 30: 3598-603.

Day, C. L., D. E. Kaufmann, P. Kiepiela, J. A. Brown, E. S. Moodley, S. Reddy, E. W. Mackey, J. D. Miller, A. J. Leslie, C. DePierres, Mncubez, J. Duraiswamy, B. Zhu, Q. Eichbaum, M. Altfeld, E. J. Wherry, H. M. Coovadia, P. J. Goulder, P. Klenerman, R. Ahmed, G. J. Freeman and B. D. Walker. 2006. PD-1 expression on HIV-specific T cells is associated with T-cell exhaustion and disease progression. Nature. 443: 350-4.

Dong, H., S. E. Strome, D. R. Salomao, H. Tamura, F. Hirano, D. B. Flies, P. C. Roche, J. Lu, G. Zhu, K. Tamada, V. A. Lennon, E. Celis and L. Chen. 2002. Tumor-associated B7-H1 promotes T-cell apoptosis: a potential mechanism of immune evasion. Nat Med. 8: 793-800.

Dunn, G. P., L. J. Old and R. D. Schreiber. 2004. The three E's of cancer immunoediting. Annu. Rev. Immunol. 22: 329-60.

Fourcade, J., P. Kudela, Z. Sun, H. Shen, S. R. Land, D. Lenzner, P. Guillaume, I. F. Luescher, C. Sander, S. Ferrone, J. M. Kirkwood and H. M. Zarour. 2009. PD-1 is a regulator of NY-ESO-1-specific CD8+ T cell expansion in melanoma patients. J Immunol. 182: 5240-9.

Gehring, A. J., Z. Z. Ho, A. T. Tan, M. O. Aung, K. H. Lee, K. C. Tan, S. G. Lim and A. Bertoletti. 2009. Profile of tumor antigen-specific CD8 T cells in patients with hepatitis B virus-related hepatocellular carcinoma. Gastroenterology. 137: 682-90.

Golden-Mason, L., B. E. Palmer, N. Kassam, L. Townshend-Bulson, S. Livingston, B. J. McMahon, N. Castelblanco, V. Kuchroo, D. R. Gretch and H. R. Rosen. 2009. Negative immune regulator Tim-3 is overexpressed on T cells in hepatitis C virus infection and its blockade rescues dysfunctional CD4+ and CD8+ T cells. J. Virol. 83: 9122-30.

Jones, R. B., L. C. Ndhlovu, J. D. Barbour, P. M. Sheth, A. R. Jha, B. R. Long, J. C. Wong, M. Satkunarajah, M. Schweneker, J. M. Chapman, G. Gyenes, B. Va li, M. D. Hyrcza, F. Y. Yue, C. Kovacs, A. Sassi, M. Loutfy, R. Halpenny, D. Persad, G. Spotts, F. M. Hecht, T. W. Chun, J. M. McCune, R. Kaul, J. M. Rini, D. F. Nixon and M. A. Ostrowski. 2008. Tim-3 expression defines a novel population of dysfunctional T cells with highly elevated frequencies in progressive HIV-1 infection. J. Exp. Med. 205: 2763-79.

Klenerman, P. and A. Hill. 2005. T cells and viral persistence: lessons from diverse infections. Nat Immunol. 6: 873-9.

Latchman, Y., C. R. Wood, T. Chern ova, D. Chaudhary, M. Borde, I. Chernova, Y. Iwai, A. J. Long, J. A. Brown, R. Nunes, E. A. Greenfield, K. Bourque, V. A. Boussiotis, L. L. Carter, B. M. Carreno, N. Malenkovich, H. Nishimura, T. Okazaki, T. Honjo, A. H. Sharpe and G. J. Freeman. 2001. PD-L2 is a second ligand for PD-1 and inhibits T cell activation. Nat. Immunol. 2: 261-8.

Monney, L., C. A. Sabatos, J. L. Gaglia, A. Ryu, H. Waldner, T. Chernova, S. Manning, E. A. Greenfield, A. J. Coyle, R. A. Sobel, G. J. Freeman and V. K. Kuchroo. 2002. Th1-specific cell surface protein Tim-3 regulates macrophage activation and severity of an autoimmune disease. Nature. 415: 536-41.

Mumprecht, S., C. Schurch, J. Schwaller, M. Solenthaler and A. F. Ochsenbein. 2009. Programmed death 1 signaling on chronic myeloid leukemia-specific T cells results in T-cell exhaustion and disease progression. Blood. 114: 1528-36.

Petrovas, C., J. P. Casazza, J. M. Brenchley, D. A. Price, E. Gostick, W. C. Adams, M. L. Precopio, T. Schacker, M. Roederer, D. C. Douek and R. A. Koup. 2006. PD-1 is a regulator of virus-specific CD8+ T cell survival in HIV infection. J. Exp. Med. 203: 2281-92.

Shin, H., S. D. Blackburn, A. M. Intlekofer, C. Kao, J. M. Angelosanto, S. L. Reiner and E. J. Wherry. 2009. A role for the transcriptional repressor Blimp-1 in CD8(+) T cell exhaustion during chronic viral infection. Immunity. 31: 309-20.

Swann, J. B. and M. J. Smyth. 2007. Immune surveillance of tumors. J. Clin. Invest. 117: 1137-46.

Thompson, R. H., S. M. Kuntz, B. C. Leibovich, H. Dong, C. M. Lohse, W. S. Webster, S. Sengupta, I. Frank, A. S. Parker, H. Zincke, M. L. Blute, T. J. Sebo, J. C. Cheville and E. D. Kwon. 2006. Tumor B7-H1 is associated with poor prognosis in renal cell carcinoma patients with long-term follow-up. Cancer Res. 66: 3381-5.

Trautmann, L., L. Janbazian, N. Chomont, E. A. Said, S. Gimmig, B. Bessette, M. R. Boulassel, E. Delwart, H. Sepulveda, R. S. Balderas, J. P. Routy, E. K. Haddad and R. P. Sekaly. 2006. Upregulation of PD-1 expression on HIV-specific CD8+ T cells leads to reversible immune dysfunction. Nat. Med. 12: 1198-202.

Urbani, S., B. Amadei, D. Tola, M. Massari, S. Schivazappa, G. Missale and C. Ferrari. 2006. PD-1 expression in acute hepatitis C virus (HCV) infection is associated with HCV-specific CD8 exhaustion. J. Virol. 80: 11398-403.

Wherry, E. J., J. N. Blattman, K. Murali-Krishna, R. van der Most and R. Ahmed. 2003. Viral persistence alters CD8− T cell immunodominance and tissue distribution and results in distinct stages of functional impairment. J. Virol. 77: 491 1-27.

Yamamoto, R., M. Nishikori, T. Kitawaki, T. Sakai, M. Hishizawa, M. Tashima, T. Kondo, K. Ohmori, M. Kurata, T. Hayashi and T. Uchiyama. 2008. PD-1-PD-1 ligand interaction contributes to immunosuppressive microenvironment of Hodgkin lymphoma. Blood. 111: 3220-4.

Zajac, A. J., J. N. Blattman, K. Murali-Krishna, D. J. Sourdive, M. Suresh, J. D. Altman and R. Ahmed. 1998. Viral immune evasion due to persistence of activated T cells without effector function. JExp Med. 188: 2205-13.

Zhang, L., T. F. Gajewski and J. Kline. 2009. PD-1/PD-L1 interactions inhibit antitumor immune responses in a murine acute myeloid leukemia model. Blood. 114: 1545-52.

Zitvogel, L., A. Tesniere and G. Kroemer. 2006. Cancer despite immunosurveillance: immunoselection and immunosubversion. Nat. Rev. Immunol. 6: 7 15-727.

We claim:

1. A method of treating a subject having a persistent infection, cancer or tumor, the method comprising administering to a subject having a persistent infection, cancer or tumor an effective amount of a multispecific polypeptide agent comprising at least one binding site that specifically binds to a PD-1 molecule, and at least one binding site that specifically binds to a TIM-3 molecule, thereby treating the persistent infection, cancer or tumor in the subject.

2. A method of activating an immune response in a subject having a persistent infection, cancer or tumor, the method comprising administering to a subject having a persistent infection, cancer or tumor an effective amount of a multispecific polypeptide agent comprising at least one binding site that specifically binds to a PD-1 molecule, and at least one binding site that specifically binds to a TIM-3 molecule, thereby activating an immune response in the subject having a persistent infection, cancer or tumor.

3. The method of claim 1, wherein the persistent infection, cancer or tumor comprises a population of functionally exhausted T cells.

4. The method of claim 3, wherein the population of functionally exhausted T cells comprises a CD8+ T cell population.

5. The method of claim 1, wherein the multispecific polypeptide agent is a multispecific antibody or a multispecific antibody fragment thereof.

6. The method of claim 1, wherein the binding site that specifically binds to the PD-1 molecule is directed against a PD-1 ligand interaction site.

7. The method of claim 1, wherein the binding site that specifically binds to the TIM-3 molecule is directed against a TIM-3 ligand interaction site.

8. The method of claim 1, wherein the subject has a cancer that comprises a population of functionally exhausted tumor-infiltrating lymphocytes.

9. The method of claim 2, wherein the persistent infection, cancer or tumor comprises a population of functionally exhausted T cells.

10. The method of claim 9, wherein the population of functionally exhausted T cells comprises a CD8+ T cell population.

11. The method of claim 2, wherein the multispecific polypeptide agent is a multispecific antibody or a multispecific antibody fragment thereof.

12. The method of claim 2, wherein the binding site that specifically binds to the PD-1 molecule is directed against a PD-1 ligand interaction site.

13. The method of claim 2, wherein the binding site that specifically binds to the TIM-3 molecule is directed against a TIM-3 ligand interaction site.

14. A method of reversing functional exhaustion of tumor-infiltrated CD8+ T cells in a tumor, the method comprising administering to a subject having such a tumor an effective amount of a multispecific polypeptide agent comprising at least one binding site that specifically binds to a PD-1 molecule, and at least one binding site that specifically binds to a TIM-3 molecule.

15. The method of claim 14, wherein the multispecific polypeptide agent is a multispecific antibody or a multispecific antibody fragment thereof.

16. The method of claim 14, wherein the binding site that specifically binds to the PD-1 molecule is directed against a PD-1 ligand interaction site.

17. The method of claim 14, wherein the binding site that specifically binds to the TIM-3 molecule is directed against a TIM-3 ligand interaction site.

* * * * *